United States Patent
Nemser

[11] Patent Number: 5,914,154
[45] Date of Patent: Jun. 22, 1999

[54] NON-POROUS GAS PERMEABLE MEMBRANE

[75] Inventor: Stuart Marshall Nemser, Wilmington, Del.

[73] Assignee: Compact Membrane Systems, Inc., Wilmington, Del.

[21] Appl. No.: 08/862,944

[22] Filed: May 30, 1997

[51] Int. Cl.⁶ ................................. B05D 7/22; B05D 5/00
[52] U.S. Cl. ..................... 427/245; 427/235; 427/238; 427/244; 427/378; 427/379; 427/381
[58] Field of Search ..................... 427/244, 245, 427/379, 378, 350, 389.9, 369, 296, 246, 235, 238

[56] References Cited

U.S. PATENT DOCUMENTS

| | | | |
|---|---|---|---|
| 3,661,621 | 5/1972 | Jager | 427/296 |
| 4,214,020 | 7/1980 | Ward et al. | 427/296 |

(List continued on next page.)

FOREIGN PATENT DOCUMENTS

| | | |
|---|---|---|
| 0649676 | 4/1994 | European Pat. Off. |
| 0641194 | 3/1995 | European Pat. Off. |
| WO 90/15662 | 12/1990 | WIPO . |

OTHER PUBLICATIONS

Lund, L. W., et al., Gas permeability of hollow fiber membranes in a gas–liquid system, *Journal of Membrane Science*, 117 (1996) 207–219. (no month).

Nemser, S., Applications of Membranes in Industry Glassy Fluoropolymer Membranes, 21st Aharon Katzir–Katchalsky Conference, Rehovot, Israel, Sep. 5–8, 1993.

Nemser, S., "Graph I" presentation at University of Pittsburgh, Pittsburgh, Pennsylvania, Feb. 27, 1996.

(List continued on next page.)

Primary Examiner—Diana Dudash
Attorney, Agent, or Firm—Jeffrey C. Lew

[57] ABSTRACT

A process for placing an ultra thin layer of a non-porous gas permeable polymer continuously over an entire filter surface area allows the fabrication of compact, high flux, fouling resistant gas filters. The process involves contacting a dilute coating solution of gas permeable polymer in a solvent with one side of a microporous substrate. The pore size of the substrate is chosen for its ability to effectively filter the gas permeable polymer from the coating solution. Solvent of the coating solution is made to flow through the microporous substrate which causes an ultra thin layer of polymer to build up on the side of substrate. When a desired thickness of polymer is built up, the solution and solvent is removed and residual solvent is evaporated, preferably by passing a gas at high rate over the surface of the polymer layer.

This process can be used to coat flat sheet and hollow fiber substrates. The process is particularly useful for coating multiple hollow fibers assembled in modules which by virtue of the high surface area density of small diameter fibers and the efficient packing of many fibers in the modules, provide very high filter surface area in a small volume. The coated fiber modules thus can be used as high flow rate gas filters in applications such as filtering nuisance particules from recovered gas streams, collecting hazardous or valuable droplets suspended in a gas process stream for protection or salvage. Specific applications include filtering air for microelectronic circuit assembly facilities and filtering microbes from the atmosphere in biomedical "clean rooms".

A preferred gas permeable polymer for use with this invention is an amorphous copolymer of perfluoro-2,2-dimethyl-1,3-dioxole. The superior hydrophobicity and oleophobicity of this material in the form of a non-porous, continuous layer provides a barrier for solid particles and liquid droplets from blocking flow through a gas filter. Furthermore, a gas filter made according to this invention can be easily cleaned and restored to near-original gas flux performance.

49 Claims, 5 Drawing Sheets

U.S. PATENT DOCUMENTS

| | | | |
|---|---|---|---|
| 4,230,463 | 10/1980 | Henis et al. | 55/16 |
| 4,243,701 | 1/1981 | Riley et al. | 427/244 |
| 4,347,204 | 8/1982 | Takagi et al. | 427/296 |
| 4,767,643 | 8/1988 | Westervelt et al. | 427/296 |
| 4,778,477 | 10/1988 | Lauchenauer | 427/296 |
| 4,840,819 | 6/1989 | Williams et al. | 427/245 |
| 4,844,871 | 7/1989 | Polaschegg | 422/81 |
| 4,857,080 | 8/1989 | Baker et al. | 427/296 |
| 4,938,778 | 7/1990 | Ohyabu et al. | 427/245 |
| 5,051,114 | 9/1991 | Nemser et al. | 55/16 |
| 5,116,650 | 5/1992 | Bowser | 428/34.2 |
| 5,238,471 | 8/1993 | Blanchet-Fincher | 96/13 |
| 5,258,202 | 11/1993 | Pellegrino et al. | 427/244 |
| 5,523,118 | 6/1996 | Williams | 427/2.31 |
| 5,554,414 | 9/1996 | Moya et al. | 427/244 |

OTHER PUBLICATIONS

"The Filtration Spectrum" Osmonics Inc., 5951 Clearwater Drive, Minnetonka MN, 1984 (no month).

Yeung, K.L., et al. Novel Preparation Techniques for Thin Metal–Ceramic Composite Membranes, AIChE Journal, vol. 41, No. 9, Sep., 1995.

Pinnau et al: J. Membrane Sci., vol. 109, pp. 125–133, 1996. no month.

NON-POROUS GAS PERMEABLE MEMBRANE

FIELD OF THE INVENTION

This invention relates to a process for producing gas permeable membranes. More specifically, the invention pertains to non-porous gas permeable membranes for separating a gas from an aerosol, and especially to fluoropolymer membrane filters for removing ultra-fine solid particles or liquid droplets suspended in gas.

BACKGROUND AND SUMMARY OF THE INVENTION

Many modern industrial processes involve contacting liquids or solids with a gas which produces a suspension of liquid droplets and/or solid particles in the gas. Frequently, the suspended substance is a hazardous or expensive material or merely is nuisance contamination in a valuable gas stream. Filtration of droplets and particles from gas thus becomes important for many commercial applications such as recovery or containment of valuable or dangerous particulate materials; venting purified exhaust gas for disposal to the environment; and purifying a contaminated gas stream for use as a raw material in a later process step.

Membrane technology increasingly is applied to the filtration of industrial gases. Because fluoropolymers have certain physical properties such as good hydrophobicity, inertness to a variety of chemical and biological materials, and good thermal stability, these materials, and especially microporous, expanded polytetrafluoroethylene ("E-PTFE"), are popular for use in porous membrane filters. One notable shortcoming is that oil "wets" E-PTFE. Wetting refers to the affinity of a liquid for the membrane material. E-PTFE can become so wet with oil that the oil clogs the pores of the membrane. This reduces and sometimes totally blocks the gas flow through the membrane. Oil is present in a large number of gas processing applications, including oil lubricated compression and automotive applications, for example. Hence, the oleophilic nature of E-PTFE significantly reduces the effectiveness of this material in membrane filtration.

A gas permeable membrane with both high hydrophobicity and oleophobicity has been sought for improved gas filtration performance. U.S. Pat. No. 5,554,414 of Moya et al. provides a process for producing a composite porous article having a porous polymeric substrate and a hydrophobic/oleophobic polymeric surface formed from a cross-linked ethylenically unsaturated monomer containing a fluoroalkyl group. The polymeric surface is formed by coating a porous membrane substrate with a solution of a polymerizable monomer, a cross-linking agent, and a polymerization initiator. The polymerizable monomer is polymerized and cross-linked onto the porous membrane substrate in a way that the entire surface of the porous membrane, including the inner surfaces of the porous membrane, is modified with a cross-linked polymer. However, the composite porous article retains substantially all of the original properties of the substrate, particularly porosity.

U.S. Pat. No. 5,116,650 of Bowser describes the use of an amorphous copolymer of 10–40 mole percent tetrafluoroethylene ("TFE") and a complementary amount of perfluoro-2, 2-dimethyl-1, 3-dioxole ("PDD") for a gas filter. The amorphous copolymer is coated onto a gas permeable material which has passageways, or continuous pores, through the material. The amorphous copolymer coats at least a portion of the interior of the passageways but does not block them.

The above-cited references describe completely porous membrane structures for gas filtration. Gas molecules can travel readily through such a structure via the passageways formed by the pores. As a result porous structures generally provide high gas flux, that is, gas transmission per unit of filter surface area. Hence, a moderately sized porous filter element usually can transfer gas at industrially acceptable rate. Although the pores are coated with enhanced oleophobic compositions to reduce the tendency of oil to adhere to the membrane, the open pores still provide the opportunity for oil to penetrate and eventually clog the membrane. Solid particles that may be suspended in a gas can also enter and occlude the pores. Additionally, penetrating liquid and solid contaminants can become embedded in the pores and can be difficult to clean out. Thus, the gas flow through a porous membrane gas filter can decrease over time in service.

A practical, non-porous permeable membrane for a gas filter has not been available previously. Gas flux through a non-porous permeable membrane is directly proportional to permeability of the membrane composition and inversely proportional to membrane thickness. Most polymeric compositions have low gas permeability. Consequently, to provide a filter element of practical size surface area with industrially significant gas flux, a non-porous membrane of even moderately high permeability would need to be extremely thin. Heretofore a method for making a sufficiently thin non-porous gas permeable membrane for a gas filter has not been known in the art.

A process for making a membrane structure comprising an ultra-thin, continuous layer of a non-porous, gas permeable polymer composition now has been discovered. The polymer composition has good permeability which provides high initial gas flux. Additionally, the non-porous structure of the continuous layer imparts superior resistance to oil and solid particle penetration and improved stability of gas flux. Furthermore, if the novel membrane structure becomes fouled, it can be cleaned easily to restore gas flux to near-original gas transmission rate. As a consequence of this invention, it is now possible to produce a very thin film of a non-porous, gas permeable polymer in a membrane structure adaptable for use as a gas filter and for other gas transfer operations.

Accordingly, this invention provides a process for making a membrane structure comprising the steps of:

(a) dissolving a gas permeable polymer in a solvent to obtain a coating solution;

(b) selecting a microporous substrate of a pore size effective for filtering dissolved polymer from the coating solution, the substrate having a first side, and a second side;

(c) contacting the first side of the microporous substrate with the coating solution;

(d) making the solvent flow through the microporous substrate to the second side;

(e) removing coating solution and solvent from the membrane structure; and (f) evaporating solvent from the membrane structure, thereby forming a continuous, non-porous layer of the gas permeable polymer on the first side.

In another aspect, the present invention also provides a process for coating hollow fibers with an ultra-thin, continuous layer of a gas permeable polymer.

Additionally, there is provided a process for making a gas filter comprising the steps of:

(a) dissolving a gas permeable polymer in a solvent to obtain a coating solution;

(b) providing a filter module including
(1) an elongated casing having two ends, the casing defining a shell side cavity;
(2) a first tube sheet at one end of the casing having a first tube sheet outboard face;
(3) a second tube sheet at the other end of the casing having a second tube sheet outboard face;
(4) a plurality of open ended, microporous hollow fibers extending in substantially parallel alignment within the casing from the first tube sheet outboard face to the second tube sheet outboard face, the hollow fibers collectively defining a tube side cavity; wherein the pore size of the hollow fibers is effective to filter dissolved polymer from the coating solution; and
(5) at least one shell side port through the casing;

(c) causing the coating solution to flow through one of the shell side cavity and the tube side cavity;

(d) making the solvent flow from the coating solution through the microporous hollow fibers to the other of the shell side cavity and the tube side cavity;

(e) draining coating solution and solvent from the module; and (f) evaporating solvent from the hollow fibers thereby forming a continuous, non-porous layer of the gas permeable polymer on one side of the hollow fibers.

In another aspect, the present invention provides a method of separating a gas from an aerosol comprising permeating the gas through a filter surface area of a membrane structure including a microporous substrate; and a non-porous gas permeable layer on the substrate and continuous over the entire filter surface area of an amorphous copolymer of perfluoro-2,2-dimethyl-1,3-dioxole having a permeability to oxygen of at least 100 barrers at a temperature below the glass transition temperature of the amorphous copolymer.

Still further there is provided a novel gas filter comprising a membrane structure having a filter surface area for permeating a gas to separate suspended droplets from the gas, the membrane structure comprising:

a microporous substrate having a pore size of about 0.005–0.1 $\mu$m; and a non-porous gas permeable layer on the substrate and continuous over the entire filter surface of an amorphous copolymer of perfluoro-2,2-dimethyl-1,3-dioxole having a permeability to oxygen of at least 100 barrers at a temperature below the glass transition temperature of the amorphous copolymer.

DETAILED DESCRIPTION

Figure 1:
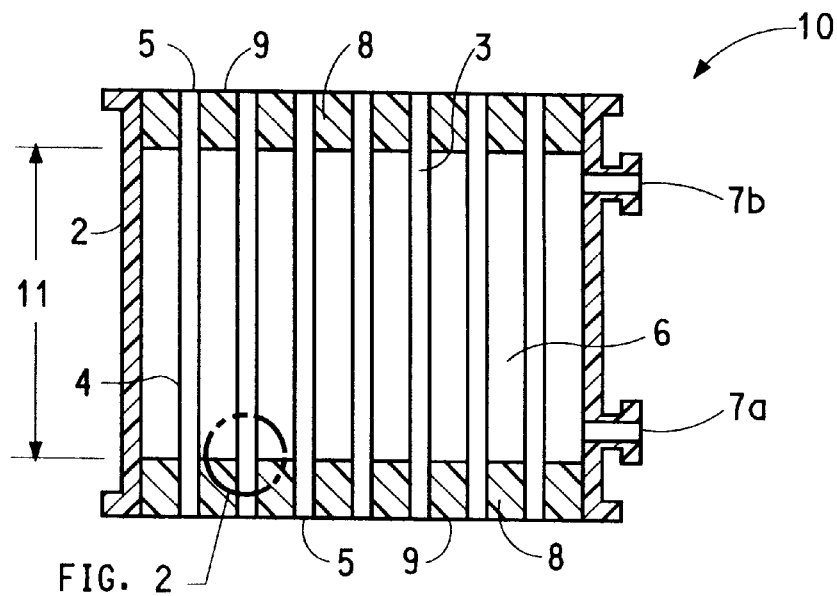
FIG. 1 is a section view of a compact hollow fiber gas filter module according to the present invention.

In one aspect, the present invention involves a method of separating a gas from an aerosol. The term "aerosol" means a suspension of fine liquid droplets or solid particles, (hereinafter, collectively, "droplets") in a gas. The invention is suitable for filtering either liquid droplets, solid particles or both simultaneously. Thus the present invention can be utilized to make a more concentrated aerosol by removing a portion of the gas or to substantially completely remove the gas for collection of the droplets. The purified exhaust gas will be substantially free of droplets, hence the invention can be used to obtain a clean gas from an aerosol.

The size of the droplets is determined by various factors. These can include system pressure and temperature, physical properties of the droplets such as composition and liquid viscosity, and the method by which the droplets are created, e.g., by condensation and by atomization. The droplets can be of uniform size or have a size distribution. Generally, the size of droplets suspended in the aerosol will lie in the range of about 0.01 $\mu$m to about 1 mm. The concentration of droplets is not critical. It should be appreciated that liquid droplets normally will coalesce on contact.

Separation is effected by filtering the gas through a gas filter which includes a gas permeable membrane structure. The nature of the gas in the aerosol is not particularly important as long as the gas can permeate the membrane structure. However, one can readily appreciate that the gas should not react with or otherwise adversely affect the materials of construction of the membrane structure or parts of the gas filter to which the gas is exposed. Representative gaseous components include elemental gases such as helium, hydrogen, neon, nitrogen, argon, oxygen, krypton and xenon; hydrocarbons such as methane, ethylene, ethane, acetylene, propane, propylene, cyclopropane, butane and butylene; halocarbons or halohydrocarbons such as dichlorodifluoromethane, methylene chloride, and methyl chloride; and miscellaneous industrial and environmental gases such as nitrous oxide, carbon dioxide, ozone, hydrogen sulfide, ammonia, sulfur dioxide, carbon monoxide, phosgene and any mixture of any of them.

One element of the membrane structure is a non-porous film of a gas permeable substance. Preferably, the gas permeable substance is an amorphous copolymer of a certain perfluorinated dioxole monomer, namely perfluoro-2,2-dimethyl-1,3-dioxole ("PDD"). In some preferred embodiments, the copolymer is copolymerized PDD and at least one monomer selected from the group consisting of tetrafluoroethylene ("TFE"), perfluoromethyl vinyl ether, vinylidene fluoride and chlorotrifluoroethylene. In other preferred embodiments, the copolymer is a dipolymer of PDD and a complementary amount of TFE, especially such a polymer containing 50–95 mole % of PDD. Examples of dipolymers are described in further detail in U.S. Pat. Nos. 4,754,009 of E. N. Squire, which issued on Jun. 28, 1988; and 4,530,569 of E. N. Squire, which issued on Jul. 23, 1985. Perfluorinated dioxole monomers are disclosed in U.S. Pat. No. 4,565,855 of B. C. Anderson, D. C. England and P. R. Resnick, which issued Jan. 21, 1986. The disclosures of all of these U.S. patents are hereby incorporated herein by reference.

The amorphous copolymer can be characterized by its glass transition temperature ("$T_g$"). The polymer property of glass transition temperature is well understood in the art. It is the temperature at which the copolymer changes from a brittle, vitreous or glassy state to a rubbery or plastic state. The glass transition temperature of the amorphous copolymer will depend on the composition of the specific copolymer of the membrane, especially the amount of TFE or other comonomer that may be present. Examples of $T_g$ are shown in FIG. 1 of the aforementioned U.S. Pat. No. 4,754,009 of E. N. Squire as ranging from about 260° C. for dipolymers with 15% tetrafluoroethylene comonomer down to less than 100° C. for the dipolymers containing at least 60 mole % tetrafluoroethylene. It can be readily appreciated that perfluoro-2,2-dimethyl-1,3-dioxole copolymers according to this invention can be tailored to provide sufficiently high $T_g$ that a membrane of such composition can withstand exposure to steam temperatures. Hence, membranes of this invention can be made steam sterilizable and thereby suitable for various uses requiring sterile materials, especially those involving biological materials. Preferably, the glass transition temperature of the amorphous copolymer should be at least 115° C.

The amorphous copolymer is further characterized by substantial hydrophobicity and oleophobicity. This incompatibility of the PDD copolymer with both water and oil also makes the gas permeable membrane not more than negligibly soluble or swellable in a wide range of liquids. This characteristic assures the preservation of the structural integrity and dimensional stability of the membrane while in contact with many liquid compositions.

The shape of the membrane structure of the present invention can be a flat sheet or other geometric configuration. A flat sheet can comprise one or more monolithic films of the non-porous, gas permeable substance. Gas flux through a permeable membrane is inversely proportional to the thickness and directly proportional to the gas transport area of the membrane. One of skill in the art will readily appreciate that to obtain a practically acceptable gas flux through a gas permeable film of reasonable surface area, a very thin film should be used. This is true even though the permeability of many commercially significant gases through the amorphous copolymer preferred for use in this invention is quite high. The preferred non-porous film thickness for desirable gas flux is about 0.01 to about 25 $\mu$m.

Polymer film of less than about 12 $\mu$m generally is non-self supporting. Thus, in a preferred embodiment, the gas permeable membrane structure of this invention comprises an amorphous copolymer present as a non-porous layer on a microporous substrate. The substrate maintains structural integrity of the non-porous layer in service. The structure of the substrate should be designed to have porosity so as not to impede the flow of the gaseous component. Representative porous substrates include a perforated sheet; a porous mesh fabric; a monolithic microporous polymer film; a microporous, hollow fiber and a combination of them.

The non-porous layer is located adjacent or directly on the microporous substrate and may be manufactured by any of a variety of methods known to those skilled in the art, including coating techniques such as dipping, spraying, painting and screeding. Preferably, the non-porous layer will be applied by a solvent coating method, and more preferably, by a novel solvent coating method suitable for placing an ultra-thin, continuous, non-porous amorphous copolymer layer onto a microporous substrate, as will be explained in greater detail, below. In context of thickness of the non-porous layer, the term "ultra-thin" means about 0.01 to about 10 $\mu$m.

The membrane structure can also have a tubular configuration. A hollow fiber is a particularly preferred form of substrate for use in the present invention. The term "hollow fiber" refers to high aspect ratio bodies with extremely small cross section dimensions. By "high aspect ratio" is meant the ratio of the fiber length to fiber cross section dimension. Although other hollow shapes are possible and are contemplated to fall within the breadth of the present invention, cylindrical hollow fibers are preferred. The fiber outer and inner diameter generally is about 0.1–1 mm and about 0.05–0.8 mm, respectively.

The separation process of this invention basically is carried out by placing the aerosol in contact with the gas permeable membrane component of a membrane structure in a gas filter and allowing the gas to permeate through the membrane Leaving the droplets in the aerosol. The term "filter surface area" means the effective area available for gas transport. Generally, the filter surface area is the gas transport area of the membrane measured normal to the direction of gas flow. For example, the filter surface area of a rectangular flat sheet membrane is the product of sheet length and width. Similarly, the filter surface area of a single, cylindrical hollow fiber is the product of the fiber length and the circumference of the cylinder.

The preference for hollow fiber substrate derives from the ability to create a very large filter surface area in a small volume, and especially, in a volume of small overall cross sectional area. The filter surface area of a hollow fiber per unit of fiber volume increases inversely with the diameter of the fiber. Thus, surface area density of individual small diameter hollow fibers is very great. Additionally, a large number of fibers can be bundled substantially parallel to the axis of fiber elongation and manifolded. This effectively pools the filter surface area to the total of the bundled individual fiber filter surface areas. Due to the fiber geometry, a total effective filter surface area of a hollow fiber bundle can be many multiples of the overall cross sectional area of the gas filter unit. Hollow fiber substrate also is preferred because the surface area very effectively contacts the aerosol. That is, aerosol flow can be directed through bundled hollow fibers in the fiber axial direction in a way that the aerosol sweeps across all of the available gas filter area. In contrast, a gas filter based upon flat sheet filter elements can have poorly purged "dead spaces" of aerosol and/or filtered gas in stagnant contact with the elements which causes a reduced rate of transfer through the filter elements. Nevertheless, an ultra-thin, non-porous layer on a flat sheet substrate according to the present invention can provide a highly effective and useful gas filter.

According to the present invention, the non-porous layer of amorphous copolymer is continuous over the entire filter surface area of the membrane. That is, the non-porous layer is coextensive with the substrate and uninterrupted, being substantially free of voids, perforations or other channels which could provide open passageways through the membrane for gaseous communication between the aerosol side and gas side of the gas filter other than by permeation. Preferably, the non-porous layer is on the aerosol side of the gas permeable membrane. It can be appreciated that the non-porous layer presents an uncompromised barrier to penetration of liquid droplets or solid particles into the micropores of the membrane. The separation process of the present invention thus provides a high flux, gas filter that resists clogging so that the high gas flux will remain stable for extended duration. Furthermore, the liquid droplets and solid particles cannot become embedded in the membrane structure because of the non-porous layer barrier. Therefore, if the filter should become fouled, it can easily be cleaned and restored to near-original gas flux performance.

In contrast to the present invention, conventional gas filters for aerosols, such as those disclosed by Bowser and Mayo et al., mentioned above, rely on a microporous structure coated with hydrophobic and oleophobic material. The mechanism for gas filtration in such filters is understood to rely on the flow of gas through narrow, tortuous but open passageways of pores across the complete thickness of the structure. The coated material does not eliminate penetration of these substances into the passageways. The resistance to clogging and stability of gas flux obtained from gas filters according to the present invention are superior to the performance of conventional filters.

Absence of passageways makes the gas filter of the present invention particularly well suited for processing gas in contact with biological fluids. The term "biological fluid" includes human and other animal natural body fluids such as blood, and other natural, synthetic or combined cell culture media. Such fluids typically contain cells and other microorganisms which tend to adhere to and grow on many substrate materials. While porous PDD copolymer membranes might resist adhesion and for a time maintain good gas flow in biological fluid systems, cells or microorganisms can grow in the pores to eventually block flow. However, the microorganisms cannot penetrate the non-porous layer of the novel gas filters. Moreover, if cell growth or other fouling occurs on the gas filter surface of the non-porous layer, the surface can be cleaned easily to restore performance as described above.

PDD-containing, amorphous copolymer has a high gas permeation selectivity, especially with respect to oxygen and nitrogen. The $O_2/N_2$ selectivity is a function of the PDD content in PDD copolymer. The oxygen/nitrogen selectivity of 50–90 mol a PDD copolymer is at least about 1.5:1. This high gas selectivity of PDD copolymer can be used conveniently to test whether the gas permeable element of the membrane structure is non-porous. For example, the membrane structure can be checked easily for absence of holes by sequentially exposing one side of the membrane structure to selected pure component gases at constant pressure. The selectivity can be determined by calculation of the ratio of individual gas fluxes. Approximately equal flux for each gas indicates that the non-porous layer may be defective (i.e., has perforations or holes). However, an appropriately high gas selectivity confirms that the gas permeable layer is non-porous. Because the non-porous, amorphous copolymer layer of this invention can be extremely thin, variability in processing technique provides the opportunity of making a defective gas permeable layer. Hence, it is helpful to assure the integrity of the non-porous layer by gas selectivity testing.

The novel gas separation method will usually be operated at about ambient temperature, but may be performed at higher temperatures. However, the gas permeable membranes that include PDD copolymer should be used at a temperature below the glass transition temperature, and especially at least 30° C. below the glass transition temperature of the amorphous copolymer used in the non-porous layer. As previously explained, PDD copolymers can have remarkably high $T_g$. Hence, the amorphous copolymer membranes used in the method of the present invention are capable of being utilized at elevated temperatures, including in some embodiments at temperatures above 100° C. The method of the present invention may be operated at relatively low temperatures, e.g., about 10° C. Of course, the gas filter should not be operated beyond the temperature service range of the substrate material.

According to this invention, a new process has been discovered which enables placing an ultra-thin layer of polymer onto a microporous substrate. The novel process can be used with any suitably high molecular weight polymer which is capable of dissolving in a low viscosity, liquid solvent. Of course, the solvent should not dissolve, react with or otherwise degrade the substrate material. As mentioned, amorphous copolymers of PDD and TFE are preferred for making wetting-resistant gas filter membrane structures. Certain "perfluoro" solvents can be used to dissolve these PDD/TFE copolymers in carrying out the novel process. Suitable perfluoro solvents include liquid compounds of highly or exclusively fluorine substituted carbon compounds or fluorocarbons containing ether oxygen linkages. Representative perfluoro solvents suitable for use in the novel process include perfluoroalkanes, such as perfluorohexane, perfluoroheptane and perfluorooctane, available from 3M Company, Minneapolis, Minnesota under the tradenames PF5060, PF5070 and PF5080, respectively, and FC-75 Fluorinert brand Electronic Liquid, also from 3M. FC-75 is a solvent of perfluoro compounds primarily with 8 carbons, believed to include 2-butyltetrahydrofuran.

The novel process includes dissolving the high molecular weight polymer in a solvent to produce a dilute, coating solution. A suitable microporous substrate which can effectively filter the polymer from the coating solution is selected. The coating solution is brought in contact with a first side of the microporous substrate. The solvent is made to flow through the microporous substrate to the second side of the substrate opposite the first side. This flow continues while a layer of high molecular weight polymer builds up on the first side. When a preselected thickness layer of polymer has built up, the solution is removed from contact with the first side. The solvent residue inside the pores and in the wet polymer layer is evaporated.

Solution concentration will depend upon process parameters such as composition of the dissolved polymer and the pore size of the microporous substrate. Preferably, the concentration of polymer in dilute solution should be less than about 1 wt %, more preferably less than about 0.5 wt %, and most preferably less than about 0.1 wt %.

By "effectively filter" is meant that the substrate is a barrier to the dissolved polymer molecules but allows the solvent to pass through. Thus, the pore size of the substrate is related to the size of the dissolved polymer molecule. That is, the substrate pore size is small enough to filter the polymer from the solvent.

A preferred technique for choosing a substrate pore size for use in the novel process takes into account the molecular weight of the gas permeable polymer and the desired gas flux of the product membrane structure. Once the gas permeable polymer is selected, the molecular size of the polymer in solution can be identified. For example, PDD copolymer typically has a molecular weight of about 600,000. A microporous filter having a molecular weight cut off ("MWCO") value of about 50,000, for example, would thus effectively filter a solution of this PDD copolymer. According to The Filter Spectrum, published by Osmonics, Inc., Minnetonka, Minn. the nominal size of an approximately 50,000 molecular weight polymer molecule on the Saccharide Type number scale is about 0.02–0.03 $\mu$m.

To verify that the substrate effectively filters the dissolved polymer, one can observe that solvent drawn through the substrate is substantially free of dissolved polymer. It is not necessary that the filtrate be absolutely free of dissolved polymer. Certain gas permeable polymers suitable for use in the present invention can have a broad molecular weight distribution characterized by a weight average molecular weight. The distribution thus will have certain high and low molecular weight fractions above and below the average molecular weight, respectively. The substrate may adequately filter most of the high molecular weight fractions and allow some portion of the low molecular weight fractions to pass through. Preferably, the filtrate is considered substantially free of dissolved polymer if the concentration of dissolved polymer in the filtrate is less than about 10 percent of concentration of dissolved polymer in the coating solution. Verification that the filtrate is substantially free of dissolved polymer can be determined in a number of ways. For example, a sample of filtrate can be quantitatively analyzed by chemical analysis for polymer, or the solvent can be evaporated from a sample of filtrate to reveal the existence of polymer residue. A preferred method of verifying effective filtration involves measuring and comparing the liquid viscosity of the filtrate to the viscosity of pure solvent. The filtrate will be deemed acceptably dissolved polymer-free if the filtrate viscosity is about the same as the viscosity of the pure solvent.

The substrate pore size should not be too small because an extremely small pore size microporous substrate can restrict the flow of gas. The lower limit of the substrate pore size preferably should be one that would provide at least about five times the gas flux of the desired non-porous polymer layer. For example, the oxygen flux of a 0.5 $\mu$m thick layer of PDD/TFE amorphous copolymer with a $T_g$ of 240° C. is about 2,000 gas permeation units ("GPU"). A gas permeation unit is defined as 1 cm$^3$/cm$^2$-sec-cm Hg×10$^{-6}$. In this case, the gas flux through the bare substrate should be at least 10,000 GPU. Polysulfone hollow fibers of pore size equivalent to 50,000 MWCO are rated for gas flux of 240,000 GPU. Therefore, in this example the minimum thickness for a layer of a PDD/TFE copolymer with a $T_g$ of 240° C. on polysulfone should be about 0.02 $\mu$m, which is equivalent to about 48,000 GPU.

The term "suitably high molecular weight polymer" can now be better understood to mean that the molecular weight of the polymer is selected to provide a molecule large enough that it can be filtered from the polymer solution by the microporous substrate. The pore size of the microporous substrate should be small enough to filter the polymer from solution. The microporous substrate should be of a pore size corresponding to a MWCO less than the molecular weight of the polymer. Preferably, the MWCO characteristic of the substrate should be at most about 50% of the polymer molecular weight, and more preferably, at most about 20% of the polymer molecular weight.

Evaporation of residual solvent can be carried out, for example, by sweeping a clean, inert gas through the membrane structure under pressure, by drawing a vacuum on the membrane structure, or by both. Evaporation continues until the membrane structure is effectively dry of solvent. Effective dryness is achieved when the flux of a gas, such as $O_2$ or $N_2$, through the membrane remains constant at a given set of permeation conditions (e.g., pressure and temperature). The excess solvent can be evaporated in either direction across the thickness of the membrane structure. However, when sweeping is employed, preferably the sweep gas is supplied to the coated side of the structure. When vacuum is used, preferably the vacuum is applied to the second side to draw residual solvent from the first side to the second side. Although, the pressure of the inert gas or vacuum is not critical, excessive pressure differential across the structure should be avoided to prevent blowing or sucking a hole through the membrane. Generally, slight pressure or mild vacuum are sufficient to complete the evaporation step within a matter of hours. Preferably, evaporation is done at ambient temperature. It is possible to evaporate at elevated temperature, provided that the substrate, the polymer and the apparatus holding the membrane structure are not adversely affected.

The flow rate of blowing gas over the non-porous layer for evaporating residual solvent is very important, especially for coating hollow fibers. The gas sweep should flow across the surface of the non-porous layer at a high rate effective to prevent the polymer from drying in non-uniform thickness on the substrate, for example in clumps. When coating inside surfaces of hollow fibers, the clumps can occlude the bore of the fibers. If a sufficiently high gas rate is used, the thickness of the non-porous layer will dry to a substantially uniform thickness over the whole substrate. One of ordinary skill in the art should be able to determine the minimum sweep gas flow rate necessary to produce uniform thickness coating without undue experimentation.

The novel process can be carried out in a single cycle or in a series of cycles. In a single cycle process, the step of drawing solvent through the microporous substrate continues until the preselected thickness of polymer is formed. Alternatively, the sequence of drawing and evaporating steps can be repeated multiple times in series. Each time a partial amount of the total thickness of polymer to be coated is achieved. The cycle repetition can be continued until the desired coating thickness builds up on the substrate.

The novel process can be applied with great advantage to coat a hollow fiber substrate. As mentioned, hollow fibers can have very high surface area density. Utilizing the present method, an entire filter surface area of a fiber can be coated with a continuous, ultra-thin layer of a non-porous gas permeable polymer. The novel process thus produces a very high surface area density tubular membrane structure because the gas permeable polymer layer is extremely thin.

Gas filters often are designed for high capacity in a small volume. That is, it is sought to achieve maximum gas flow with minimum pressure drop across the filter while maintaining small overall filter cross section dimensions. The coating process of this invention further provides for the ability to fabricate a module containing a plurality of closely packed, coated hollow fibers for use as a gas filter. Hence, the present invention presents the additional advantage of providing for construction of a very high capacity, compact gas filter.

Many shapes of the module are possible, however, a generally cylindrical configuration is preferred. A cylindrical gas filter is easy to make and can be fit into existing processes quite simply, often by connecting the module between flanges in a pipeline. The circular cross module between flanges in a pipeline. The circular cross section of a cylindrical gas filter additionally provides the ability to pack a large number of fibers per unit of overall filter cross sectional area. Hence, a very large number of fibers can be packed together to produce a relatively compact but extremely high surface area gas filter. For example, a coating on the outside of a 250 $\mu$m outside diameter polypropylene hollow fiber yields a gas transport area per unit volume of 16.4 cm$^2$/cm$^3$ with a fiber packing density of 40%. Packing density refers to the cross sectional area of all the fibers as percentage of the overall cross sectional area of the gas filter. For a cylindrical gas filter, the cross section is measured perpendicular to the cylindrical axis. In contrast, the typical area density for a flat sheet geometry membrane structure is only 1.1 cm$^2$/cm$^3$ or one sixteenth of packed hollow fibers.

Additionally, the amorphous copolymer used in the present invention also has very high permeability. For example, PDD/TFE copolymer membranes exhibit a permeability for oxygen of at least 100 barrers, especially at least 200 barrers and in particular at least 500 barrers. Consequently, the present method provides a gas filter with superior gas flux compared to conventional methods due to the combination of high gas permeability and ultra-thin layer of the non-porous membrane composition, and to the high filter surface area present in a compact space.

A compact hollow fiber gas filter module suitable for use in the present invention is illustrated in FIG. 1. The filter module 10 has a generally elongated cylindrical casing 2 housing a plurality of hollow fibers 4. The fibers are held in place by tube sheets 8. The fibers extend through the tube sheets allowing open ends 5 to emerge on the outboard faces 9 of the tube sheets. The effective filter surface area of each fiber is defined by the fiber diameter and by the length 11 between tube sheets.

Figure 2:
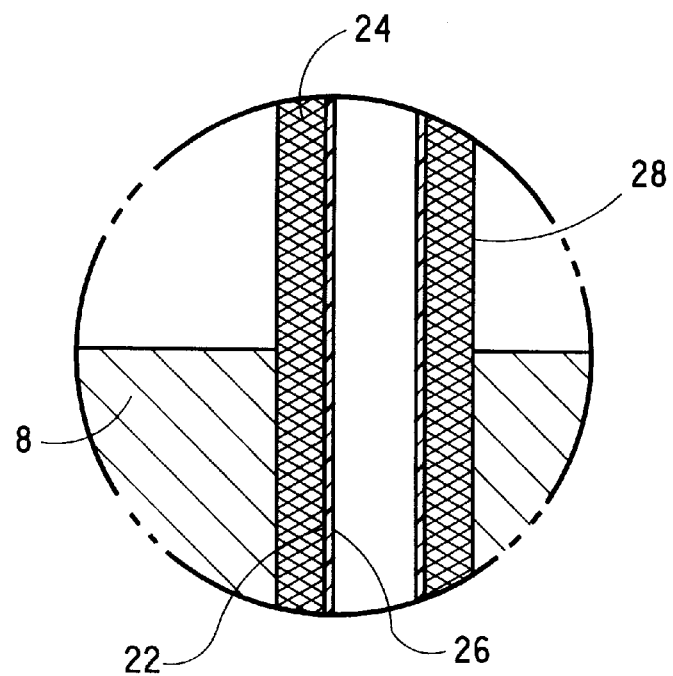
FIG. 2 is a detail view of a portion of the gas filter module of FIG. 1.

FIG. 1 shows the fibers as being perfectly parallel. This is an ideal condition which need not, and usually, is not satisfied in practice. Owing to the extremely high length-to-diameter aspect ratio and the polymeric composition, each fiber is quite flexible. It is acceptable that the fibers are aligned substantially parallel, provided that space between neighboring fibers is effective to permit gas contact with a major fraction of the outer surface of all fibers. The interior of the casing, the outside of the fibers and the inboard surfaces of the tube sheets defines the shell side cavity 6. At least one port 7a, 7b through the casing is provided to allow flow into or out of the shell side cavity. Occasionally, the module is installed in a gas filter with covers (31, 32 in FIG. 3) attached over the outboard faces of the tube sheets. The covers define inlet and outlet chambers which serve to conduct fluid into and out of the tubes. The space inside hollow fibers and within the inlet and outlet chambers, where applicable, is referred to as the tube side cavity. In the illustrated embodiment, FIG. 2, the interior gas filter surface 22 of the each fiber 24 is coated with a layer 26 of gas permeable polymer. In a contemplated alternative embodiment not shown the gas permeable layer can be coated onto the exterior surface 28 of the fiber. FIG. 2 shows that the fiber is firmly embedded into the tube sheet which provides a fluid tight seal between the shell side cavity and the tube side cavity.

Hollow fiber modules can be fabricated from fibers of various materials. Hollow fibers are available from Spectrum, Inc., Laguna Hills, Calif., and Hoechst Celanese Company, for example. A preferred method for mounting the fibers in tube sheets involves aligning a bundle of fibers and fixing the bundle together as a unit in a deep bed of thermoplastic or thermosetting cured polymer such as polyurethane. Another bed of cured polymer is used to secure the bundle at a distance (11 in FIG. 1) along the fibers from the first. A flat tube sheet outboard face can be made by cutting through one fixed bundle in a direction perpendicular to the axes of the fibers. At a convenient distance from the first outboard face, a cut through the other fixed bundle can be made to create the second outboard face. Finally, the tube bundle with tube sheets can be glued or otherwise sealed to the ends of an elongated casing to form the module. The method of making modules suitable for use in the present invention containing bare hollow fibers, i.e., fibers without a non-porous ultra-thin gas permeable layer, is known to those of skill in the art. Modules containing multiple uncoated hollow fibers are commercially available from such manufacturers as Spectrum, Inc. and Hoechst Celanese.

Figure 3:
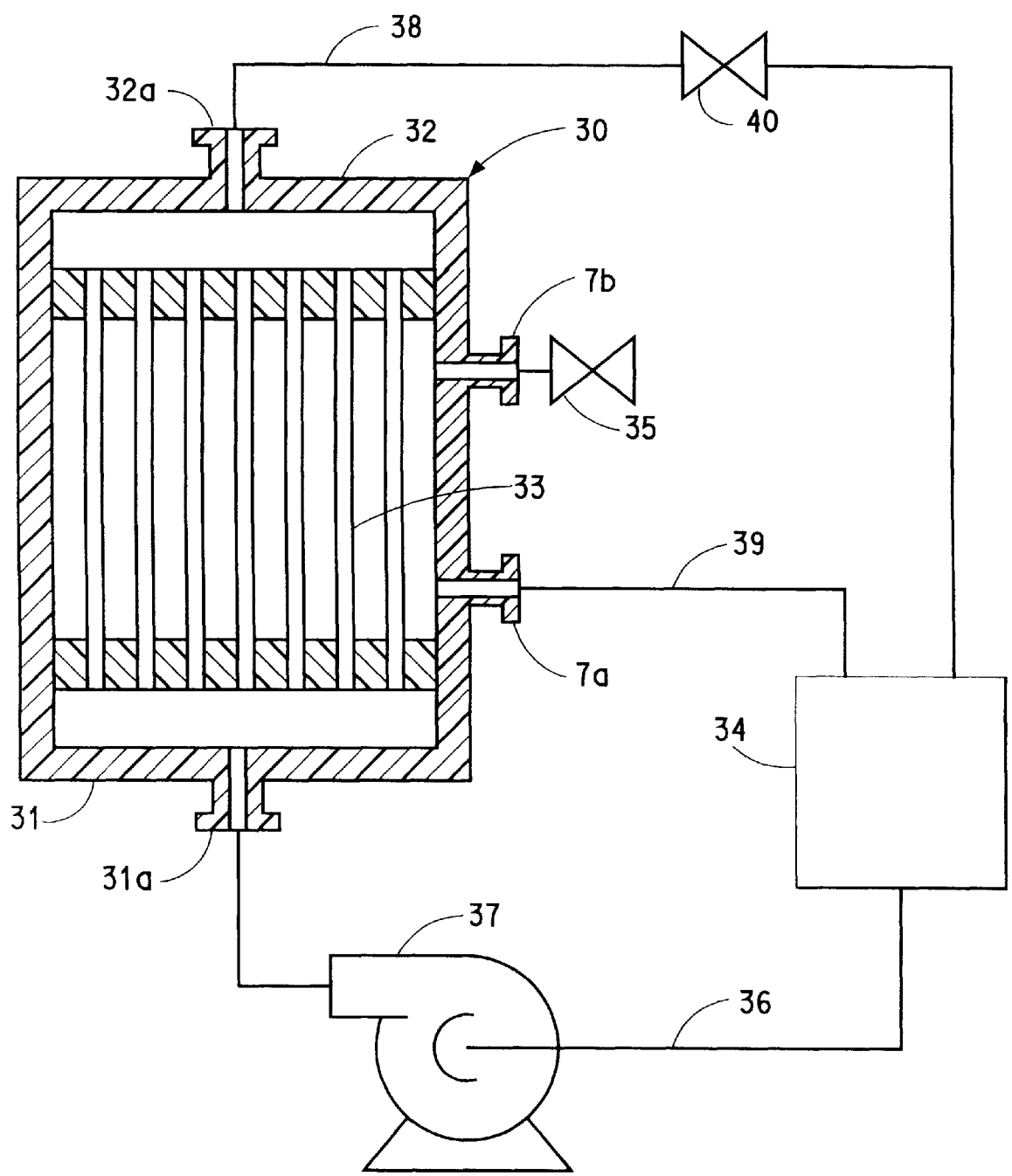
FIG. 3 is a schematic diagram of an apparatus useful for coating a thin layer of gas permeable polymer onto hollow fibers of a gas filter module according to the process of the present invention.

Operation of the novel process of coating hollow fibers can be understood with reference to FIG. 3. An uncoated hollow fiber cylindrical module 30 is equipped with tube side cavity covers 31 and 32. The covers have ports 31a and 32a, for conducting fluid to and from the tube side cavity. In the illustrated embodiment, the module is placed in an upright orientation so that the longitudinal axes of the substantially parallel aligned hollow fibers 33 are vertical. The upright orientation of the fibers has been found to be preferred for achieving the desired result of a uniformly thin coating on the inside of the fibers. The bottom tube side port of the module is connected to a feed tank 34 by feed line 36. Pump 37 is used to pump polymer solution from the feed tank through the tube side cavity. Excess tube side fluid is returned to the feed tank from top tube side port 32a through discharge line 38 and throttling valve 40. Normally, upper shell side port 7b is closed with a line blank (not shown) or with a valve 35. Fluid from the shell side cavity also returns to the storage tank through overflow line 39.

Polymer solution is recirculated by pump 37 from tank 34, through the tube side cavity of module 30 and back to the tank. Throttle valve 40 is adjusted to impose a slight pressure on the tube side cavity. This forces solvent to permeate the microporous hollow fibers which causes a layer of gas permeable polymer to build up on the interior of the fibers. When a preselected thickness of polymer layer has built up, recirculation is stopped and all fluid is drained from the tube and shell side cavities. Finally, a sweep of high flow gas is blown through the tube side to evaporate residual solvent.

Initially a dilute polymer solution is prepared by dissolving gas permeable polymer in a suitable solvent. In one way of operating the process, the amount of polymer and solution is calculated in advance from the desired tube side coating thickness. That is, the total gas filter surface area is calculated from the dimensions of the hollow fibers and from the module manufacturer specifications. The amount of polymer needed to effect a selected thickness of coating can then be calculated. A solution containing at least the calculated amount of polymer is charged to a feed tank. The actual coating thickness can be determined empirically at conclusion of the process.

The foregoing process description pertains to coating the inside surfaces of the hollow fibers with gas permeable polymer. Coating the outside surfaces of the fibers is contemplated as another embodiment of the present invention. The apparatus of FIG. 3 can be used to coat the external fiber surfaces by recirculating the polymer solution through the shell side cavity. This may be accomplished by pumping solution into lower shell side port 7a and out of upper shell side port 7b through valve 35. Similarly, top tube side cover port 32a is blanked or valved closed and permeate solvent is routed back to the storage tank through bottom tube side cover port 31a. Tubes 36, 38 and 39 and pump, 37, are re-connected to the ports as appropriate to achieve fluid recirculation.

A hollow fiber module gas filter with a gas permeable polymer coating on the tube side of the fibers according to the present invention can be used as follows. An aerosol, for example can be caused to flow through the tube side cavity. A source of the aerosol is connected to the tube side inlet port and the aerosol is permitted to enter the inlet cover, pass through the coated interior of hollow fibers, discharge to the tube side outlet cover, and exhaust through aerosol outlet port to a collection reservoir. The tube side outlet port can be closed completely to dead-end the tube side cavity or restricted partially. It can be seen that the filtered gas component will migrate through the coating of amorphous copolymer to ultimately reach filtered gas outlet port on the shell side for collection.

It can readily be appreciated that many variations in the modes of operation, number, shape and placement of module elements are suitable for use in the present invention. For example, the non-porous layer of amorphous copolymer can be placed on the exterior, shell side of the hollow fibers. In that case, preferably the aerosol would flow through the shell side of the module and the filtered gas would flow through the tube side. The drain port can be used to remove accumulated solid or precipitated liquid that is filtered from the aerosol over time.

Preferred applications for the present invention include providing contaminant-free gas for clean room environments, such as in microelectronic equipment manufacturing facilities, automotive filtration and in biological material processing facilities. The novel gas filters can also be used to recover fine chemical contaminants in gases vented from chemical processes prior to emitting the gases to atmosphere.

This invention is now illustrated by examples of certain representative embodiments thereof, wherein all parts, proportions and percentages are by weight unless otherwise indicated. Unless otherwise stated or the contrary is evident from context, all pressures referred to herein are relative to atmospheric pressure. Units of weight and measure not originally obtained in SI units have been converted to SI units.

EXAMPLES

Materials used in the examples, below, include the following:

| | |
|---|---|
| Polymer A | Teflon ® AF 2400 (E. I. du Pont de Nemours and Co., Wilmington, Delaware), dipolymer of 85 mole % perfluoro-2,2-dimethyl-1,3-dioxole and 15 mole % tetrafluoroethylene, glass transition temperature 240° C. |
| Polymer B | Teflon ® AF 1600 (E. I. du Pont de Nemours and Co., Wilmington, Delaware), dipolymer of 65 mole % perfluoro-2,2-dimethyl-1,3-dioxole and 35 mole % tetrafluoroethylene, glass transition temperature 160° C. |
| E-PTFE | Expanded polytetrafluoroethylene |
| O-1 | SAE 10W-30 automotive motor oil from Quaker State |
| O-2 | Vacuum pump oil from Norton Petroleum Co., Newark, Delaware |

Example 1 and Comparative Examples 1–4

A 0.025 wt % coating solution of Polymer B in FC-75 was prepared. Approximately 8.9 cm×20 cm of microporous E-PTFE rectangular sheet from W. L. Gore and Associates, Elkton, Md., designation Goretex® No. X19290-BAG 10F2, with nominal 0.05 µm pore size was laid onto a clean glass plate with a narrow side in the 12 o'clock ("top") position. The E-PTFE sheet thickness was about 127 µm thick. The sheet was adhered to the plate with pressure sensitive tape placed along the top edge. The sheet was placed in a transparent box purged with nitrogen gas to minimize contamination during coating. FC-75 was placed on the sheet to saturate the sheet. Excess solvent and possible air pockets were removed by drawing a rubber squeegee from top to bottom over the sheet while applying slight pressure. A bead of coating solution was laid on the sheet at the top edge and a 254 µm deep casting bar was drawn down smoothly from the top of the sheet. The coating was allowed to dry for 1 hour at room temperature. Thereafter, the coated sheet was placed for 15 hours in a vacuum oven at 50° C. and purged with 10 cm³/min. of nitrogen gas.

A portion of the uncoated, E-PTFE sheet (Comparative Example 1) was placed in a membrane holder and the rates of oxygen and nitrogen through the sheet were measured separately. From the gas flux measurements shown in Table I, the $O_2/N_2$ selectivity was calculated. Similarly, the gas flux and selectivity of the Polymer B-coated E-PTFE sheet (Comparative Example 2) was determined. Oils O-1 and O-2 were deposited separately on samples of the sheets Comp. Ex. 1 and 2 substantially in accord with the procedure described under "Visual Oil Wetting" of U.S. Pat. No. 5,116,650, incorporated herein by reference. Without blotting, observations of the wetting characteristics were made as described in Table II. Prior to contact with oil, the sheets were a uniformly light color. Wetting was visually observable as discoloration of the sheet to a contrasting gray color in the area of wetting. After 24 hours, the flat surface of the wetting test samples were tilted to a 45° angle from horizontal. The tendency of the oil drop to roll down the inclined plane was viewed as indicating whether the oil had wet the sheet. A 0.01 wt % solution of Polymer A in FC-75 was prepared. The Polymer A solution was used to coat a fresh rectangular sheet of the E-PTFE (Comparative Example 3) as described for Comp. Ex. 2.

The procedure for making the coated flat sheets was repeated with a 0.2 wt % solution of Polymer A used to coat a sheet of microporous polysulfone from Memtec of San Diego, Calif. The porosity of the polysulfone substrate had a MWCO rating of 100,000. The selectivity and oil wetting of uncoated polysulfone substrate (Comparative Example 4) and coated polysulfone (Example 1) were determined as above.

Lower individual gas fluxes of both Comp. Examples 2 and 3 in relation to corresponding gas fluxes of Comp. Ex. 1 indicates that the coating on the E-PTFE somewhat reduced the pore size of the substrate. However, the fact that the selectivity for $O_2$ and $N_2$ remained close to unity verifies that the pores remained open after coating. Polymers A and B have a high $O_2/N_2$ gas selectivity. Ex. 1 demonstrates the preferential permeability of oxygen over nitrogen through Polymer A by about two times and verifies that the polysulforne coating was non-porous and continuous over the whole substrate.

Table II shows that the non-porous membrane structure of Ex. 1 was much more resistant to oil wetting than the porous coated E-PTFE structures. Coating E-PTFE did improve oil resistance relative to uncoated E-PTFE (Comp. Ex. 1). However, within only a few minutes after depositing oil on the substrate of Comp. Ex. 2, the drop began to the wet membrane structure as evidenced by a spreading gray spot. Comp. Ex. 3 was more resistant to oil wetting but after about 3.25 hours of contact, a significant area under the drop became wet. The non-porous coating of Polymer A (Ex. 1) dramatically improved oil wetting resistance in comparison to Comp. Ex. 4. No visual evidence of wetting was observed after 3.25 hours. Furthermore, the drops of oil on the non-porous coated polysulfone rolled freely down the inclined flat structure while the oil drops on the most resistant porous coated E-PTFE sample refused to move. After 168 hours, Ex. 1 still evidenced resistance to the oil drops. This behavior further indicates that the non-porous coated membrane structures are significantly more oil resistant than the conventional structures.

TABLE I

|  | $O_2$ flux (GPU × $10^{-3}$) | $N_2$ flux (GPU × $10^{-3}$) | $O_2/N_2$ selectivity |
|---|---|---|---|
| Comp. Ex. 1 | 207 | 248 | 0.83 |
| Comp. Ex. 2 | 185 | 211 | 0.87 |
| Comp. Ex. 3 | 213 | 239 | 0.89 |
| Ex. 1 | 4.6 | 2.4 | 1.88 |
| Comp. Ex. 4 | 1,653 | 1,797 | 0.92 |

TABLE II

Observations of Oil Wetting

| Elapsed Time | Comp. Ex. 1 Uncoated E-PTFE | Comp. Ex. 2 Polymer B/ E-PTFE | Comp. Ex. 3 Polymer A/ E-PTFE | Ex. 1 Polymer A/ Polysulfone | Comp. Ex. 4 Uncoated Polysulfone |
|---|---|---|---|---|---|
| Exposure to oil O-1 | | | | | |
| 0 | 0.5 cm diam. mound shaped drop; sheet gray under drop | 0.5 cm diam. nearly spherical drop; no grayness | nearly spherical drop; no grayness | — | — |
| 1–3 min. | — | gray dots appeared under drop | — | Mound shaped drop but no grayness underneath | drop flattened and was absorbed into gray circle within 3 minutes |
| 25 min. | 0.9 cm diam. lower mound; 1 cm diam. gray circle extending outward from drop | drop still nearly spherical; 0.75 cm diam. gray circle under drop | same as time 0 | ditto | |
| 90 min. | lower mound; 1.15 cm diam. gray circle | ditto | nearly spherical drop; gray dots appeared under drop | ditto | |
| 195 min. | 1.2 cm gray circle | nearly spherical drop; gray circle diam. 0.98 cm | nearly spherical drop; 30% of area under drop was gray | ditto | |
| 24 hours | — | — | drop did not move down 45° incline | drop freely rolled down incline immediately | — |
| Exposure to O-2 | | | | | |
| 1–3 min. | same as for O-1 | same as for O-1 | same as for O-1 | Mound shaped drop but no grayness underneath | same as for O-1 |
| 25 min. | same as for O-1 | same as for O-1 | same as for O-1 | ditto | same as for O-1 |
| 90 min. | same as for O-1 | same as for O-1 | same as for O-1 | ditto | same as for O-1 |
| 195 min. | 1.33 cm gray circle | same as for O-1 | same as for O-1 | ditto | same as for O-1 |
| 24 hours | — | — | drop did not move down 45° incline | drop freely rolled down incline immediately | — |

Example 2

To 900 ml (1620 g) of FC-75 in a glass bottle was added 16.38 g of "Polymer A"). The bottle was capped and shaken by hand for about 10 minutes and then placed on a roll mill under a heat lamp overnight. A 1 wt % stock solution of Polymer A was thus produced. A 0.1 wt % coating solution was made by adding 810 ml of FC-75 to 90 ml of the 1 wt % solution in a clean glass bottle and shaking by hand for about 5 minutes. The dilution of stock solution was repeated to provide an ample supply of coating solution.

A standard "Krosflo" hollow fiber module (Spectrum, Inc., Laguna Hills, Calif., part No. K25S 100 01N, with a 6.35 cm inner diameter polysulfone casing and about 5087 polysulfone hollow fibers of 460 μm inner diameter×640 μm outer diameter and pore size rated at 50,000 MWCO was modified by the manufacturer by removing the finger webs on the shell side ports. The overall length of the fibers was 22.86 cm with 19.05 cm effective length. The modified hollow fiber module was mounted in vertical orientation substantially as shown in FIG. 3. The upper shell side port 7b was blanked closed. Transparent covers were placed on the ends of the fiber module. The 3.8 cm nominal diameter top and bottom tube side ports 31a and 32a and lower shell side port 7a were reduced with transparent barbed tubing adapters to receive nominal 79 mm inner diameter platinum-cured silicone rubber tubing. A "Masterflex L/S Quickload" peristaltic pump driven by a 6–600 rev./min. variable speed motor was placed about 15.25 cm below bottom tube side port 31a. Silicone rubber tubing was used to connect the module and pump with a 2L capacity, low density polyethylene carboy serving as feed tank in the configuration depicted in FIG. 3.

Initially 1800 ml of 0.1 wt % coating solution was charged to the feed tank. The pump was started to establish flow from the feed tank to the bottom tube side port of the module. The bottom and top ends of the fibers within the module were visually monitored through the transparent covers. Flow rate was set such that the time elapsed from when the solution first flowed into all the fibers until solution overflowed from the top of the fibers was 15 seconds. After level of solution in the feed tank dropped due to filling the module, 400 ml more coating solution was added to the tank. At selected times after flow from the top of the tubes was established, flow from the lower shell side port was diverted and the time required to collect 25 ml of permeate was determined. Flow through discharge tube 38 was throttled by appropriate loosening or tightening of hose clamp 40 with a goal of maintaining collection time of 25 ml of permeate between 8 and 15 seconds. Actual measurement and collection times are shown in Table III.

TABLE III

| Measurement Time (min:seconds) | 25 ml Collection Time (seconds) |
|---|---|
| 1:40 | 27 |
| 2:45 | 23 |
| 5:00 | 8 |
| 7:30 | 10 |
| 8:45 | 8 |

Viscosity of the permeate was measured with a cross arm No. 191 viscometer from Technical Glass Products, Inc. (Dover, N.J.). Time for the standard amount of permeate to flow through the viscometer was 225.66 seconds. FC-75 flows through the viscometer in the range of 225–228 seconds. A 0.1 wt % solution of Polymer A requires 325 seconds to flow through the same viscometer. These measurements confirm that the permeate is substantially free of dissolved polymer and that the microporous substrate effectively filtered the polymer from solution.

The pump was stopped after 10 minutes of solution recirculation. Supply line tubing was clamped below the bottom tube side port with a hemostat and severed below the hemostat. The top tube side port tubing was also cut. The module was tilted to drain permeate from the shell side into the feed tank. Polymer solution from the tube side was drained into a clean beaker by unclamping the hemostat. The module was remounted in vertical orientation and a low pressure nitrogen gas supply was connected to the top tube side port. Nitrogen was purged through the tube side of the module at a rate of 30 L/min. for 5.5 hours. At several random times, the module was temporarily tilted to empty the shell side of any accumulated liquid.

The thickness and gas selectivity of Polymer A on the fibers was determined as follows. The permeabilities of pure gases through Polymer A were determined from previously prepared tabulations. The tabulated data had been obtained from measurements of flow rate of pure gases through uniformly thick, monolithic membranes of Polymer A produced as describe in U.S. Pat. No. 5,051,114, which is incorporated herein by reference. One of the two top tube side cavity ports and one of the two shell side cavity ports were closed. A pure gas was admitted to open tube side cavity port at about 25° C. and slightly positive pressure. The gas was permitted to permeate through the coated hollow fibers and was directed from the open shell side cavity port to a calibrated burette. The flow rate was measured by observation of the displacement of a soap bubble in the burette. The average thickness of the coating on the hollow fibers was calculated to be 0.1 μm from the known permeability, the filter surface area of the module and the gas flow rate. The flow rate measurements were conducted for each of pure oxygen and nitrogen, separately. By dividing the oxygen flow rate by the nitrogen flow rate the $O_2/N_2$ selectivity was determined to be 1.90. This example demonstrates a method of coating the entire filter surface of hollow fibers with an ultra thin layer of an amorphous copolymer.

Example 3

A 0.025 wt % coating solution of Polymer A was made by adding 877.5 ml of FC-75 to 22.5 ml of the 1 wt % stock solution prepared in Example 2 in a clean glass bottle and shaking by hand for about 5 minutes. Dilution of the stock solution was repeated to provide an ample supply of coating solution.

A new "Krosflo" hollow fiber module identical to the one used in Example 2 was mounted vertically. The module 41 was connected to a solution circulation system shown schematically in FIG. 4. The same pump and feed tank as in Example 2 were used. The upper shell side port was blanked closed. The lower shell side port was connected via tubing 42 to a 1000 ml capacity KIMAX filter flask 43. The vapor space of the filter flask was vented through exhaust tube 44 to a vacuum source (not shown) consisting of a 36.8 cm long by 3.8 cm inner diameter two-piece vacuum trap submerged in ice and a Welch Duo-seal laboratory vacuum pump. Air was bled into the trap with an adjustable valve (not shown) to control the filter flask at a selected pressure.

Initially 1800 ml of the coating solution was charged to the feed tank. Pressure of the filter flask was set to a vacuum of 7.5 cm Hg absolute. The solution circulation pump was started which caused flow of coating solution into the bottom of the module. Solution flow was set at a rate such that the elapsed time to fill the fibers was 15 seconds as observed by visual inspection. Permeate began to collect in the filter flask. An additional 700 ml of coating solution was charged to the feed tank after the coating solution inventory level dropped sufficiently to make room. Viscosity of the permeate was checked as in Example 2 and found to be the same as the viscosity of FC-75. One hundred five seconds after the fibers had filled, pressure was adjusted to control filter flask vacuum at 3.8 cm Hg absolute. Two hundred ten seconds after the fibers had filled, the feed tank had emptied and the solution circulation pump was stopped. The module was disconnected from the solution apparatus and drained of liquid. The fibers were dried with 30 L/min. nitrogen purged through the tube side for 5.5 hours as in Example 2. By the measurement methods described in Example 2, the average thickness and the $O_2/N_2$ selectivity of the Polymer A layer on the hollow fibers were found to be 0.1 μm and 1.84, respectively.

Examples 4–6

The procedure for coating the inside surface of hollow fibers as described in Ex. 2 was repeated with the following changes. A 2.54 cm diameter Spectrum hollow fiber module No. M15S26 O/N with about 361 fibers of 14.2 cm effective length providing a total of 680 cm² filter surface area was used. Oxygen and nitrogen fluxes and selectivity of the membrane structures were determined and are shown in Table IV. These examples demonstrate that a small overall cross section gas filter can be made according to the present invention with a continuous, ultra thin layer of gas permeable membrane to provide high gas flux.

TABLE IV

Coated Fiber Module Performance

|       | $N_2$ flux (GPU) | $O_2$ flux (GPU) | $O_2/N_2$ Selectivity |
|-------|------------------|------------------|----------------------|
| Ex. 4 | 2,060            | 3,976            | 1.93                 |
| Ex. 5 | 2,657            | 4,862            | 1.83                 |
| Ex. 6 | 2,200            | 4,136            | 1.88                 |

Example 7 and Comparative Example 5

Figure 5:
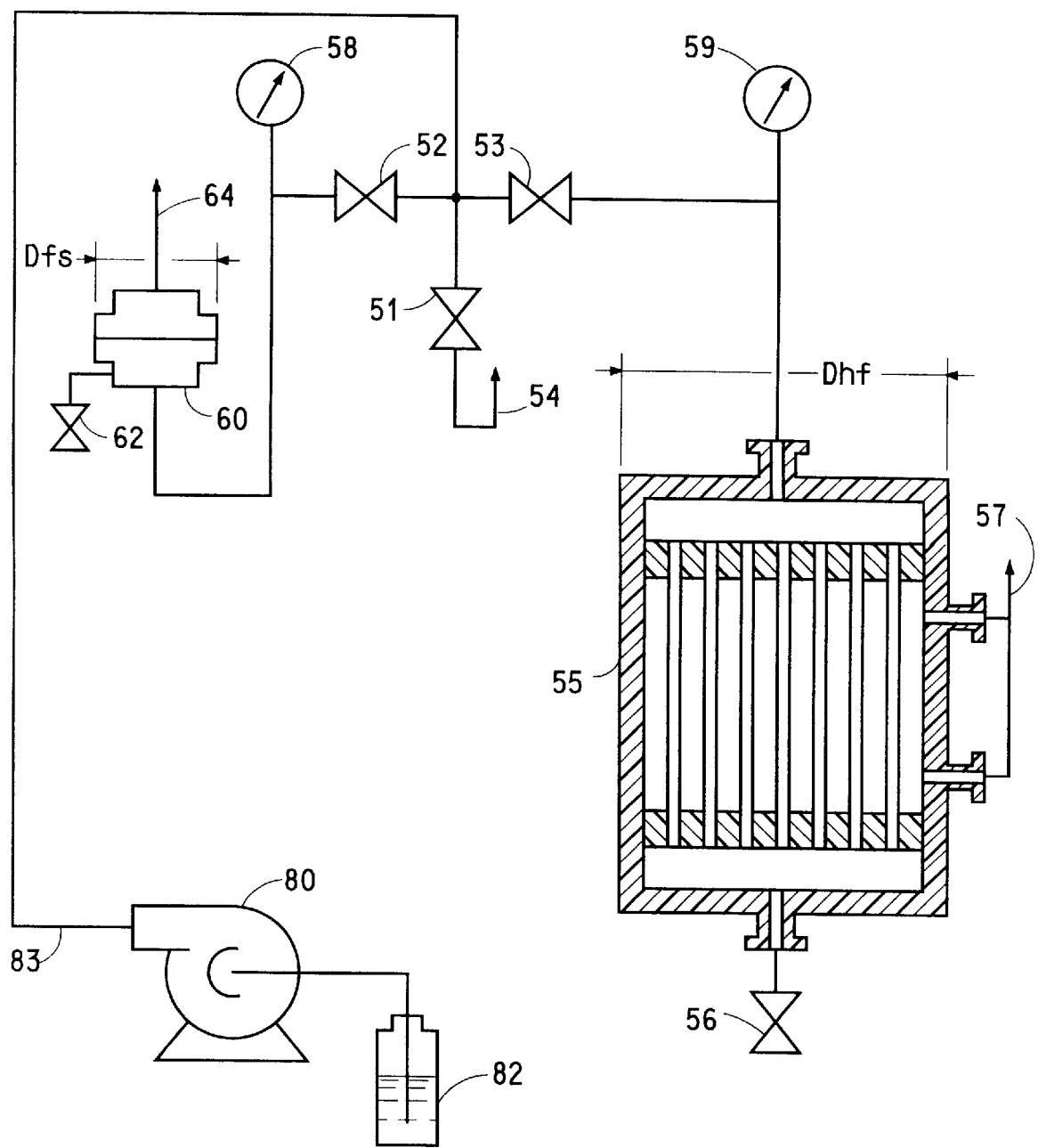
FIG. 5 is a schematic diagram of an apparatus for testing the wetting resistance of gas filters containing membrane structures.

The cylindrical, coated hollow fiber module of Example 4, identified by reference number 55 was connected-to a testing apparatus shown in FIG. 5 (Example 5). The overall cross sectional area of the module based on cylinder diameter Dhf was 5.1 cm². The filter surface of this module was 680 cm².

A centrifugal pump 80 was equipped with an oiler 82 consisting of a wick immersed in a container of O-2 oil. The wick was connected to the suction side of the pump which caused oil droplets to suspend in pump discharge air 83. Air was taken in at the pump suction and blown through valve 51 to an ambient vent through line 54. A portion of the oil-bearing air was diverted through manual control valve 52 and into a flat sheet membrane holder 60. Excess oil-bearing air was vented from the membrane holder through a line containing a manual valve 62. Air that permeated through the membrane in the holder was exhausted through tube 64 which was capable of being connected to the bottom of a glass, graduated cylinder, not shown. Soap solution was introduced into the graduate cylinder to measure volumetric flow rate of the permeate using conventional, expanding bubble technology. Another portion of the pumped air was diverted through manual control valve 53 into the top of the tube sheet cavity of fiber module 55. Excess oil-bearing air passed through the tubes and discharged through a line containing a manual valve 56. The permeate air from both upper and lower shell side ports was exhausted through common vent 57 which also was adapted to connect to a soap bubble gas flow measuring cylinder.

Figure 6:
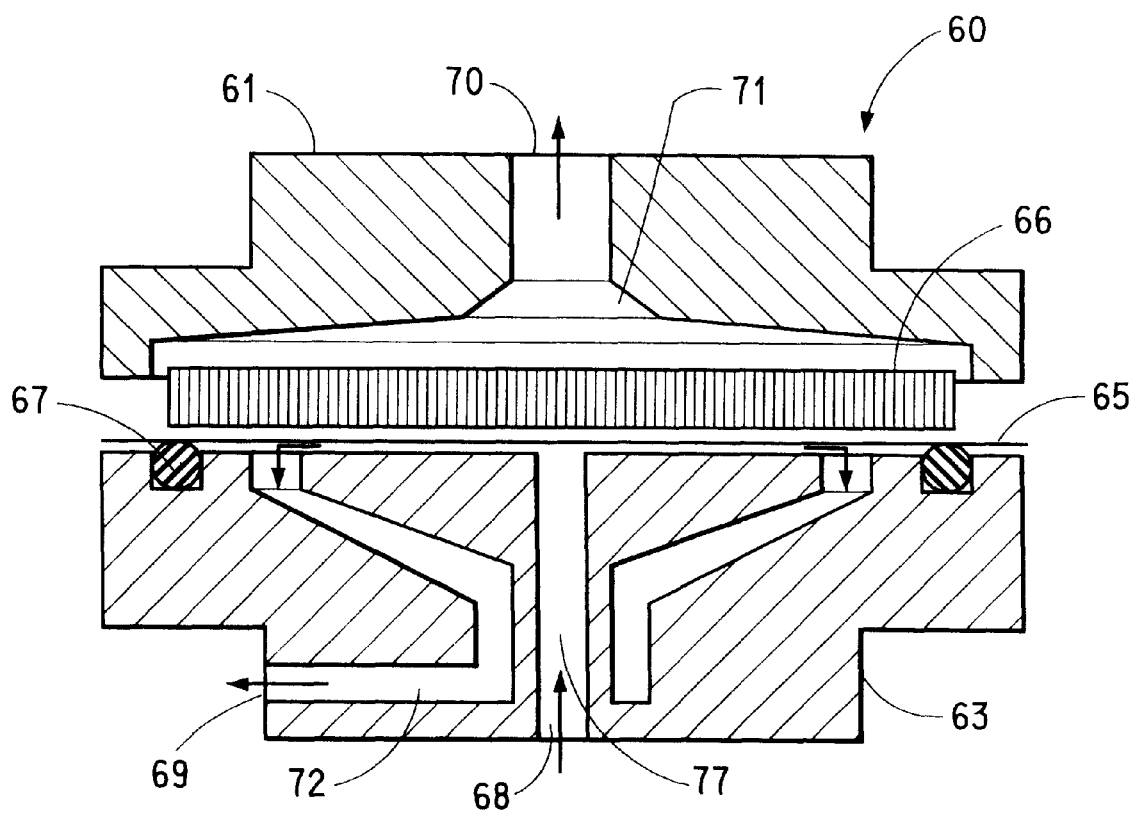
FIG. 6 is a section view of the flat sheet membrane holder 60 of FIG. 5.

A sectional schematic view of the 47 mm diameter, Dfs, circular flat sheet membrane holder 60 from Millipore Corporation, Bedford, Mass. is shown in FIG. 6. Overall cross sectional area of the flat sheet membrane holder was 17.3 cm² and the total filter surface area of the membrane was 9.6 cm². The holder includes a top block 61 and a bottom block 63 which mate to enclose a gas permeable membrane 65 and a rigid, perforated backup plate 66. The bottom block is machined to define an internal channel 77. Gas to be filtered was fed through inlet opening 68. All ports were equipped with tubing connections, not shown. The incoming air traveled in the direction of the arrow toward the membrane. The air was diverted into a narrow space adjacent to the membrane and collected in an outlet channel 72 that discharged through port 69. Permeate air discharged from space 71 through port 70 in the direction shown by the arrow. The permeate air was separated from the incoming air by the membrane and an elastomeric O-ring 67.

A 47 mm diameter circular section of the coated membrane from Comp. Ex. 2 was placed in the flat sheet membrane holder with coated side toward the incoming gas (Comparative Example 5). Pump 80 was started causing oil-bearing air to flow to vent position 54 through valve 51. Excess oily air discharge valves 56 and 62 were closed. Manual valves 52 and 53 were opened to admit oily air to the flat sheet membrane and to the hollow fiber module, respectively. The valves were adjusted to provide 2 L/min of gas through each discharge line 64 and 57. The pressure on gauges 58 and 59 and corresponding flow measurements were recorded periodically. This experiment thus exposed the novel gas filter and the conventional, flat sheet membrane to the same concentration of oil in gas. Data from the experiment are tabulated in Table V.

TABLE V

| Elapsed Time (hours) | Comp. Ex. 5 Pressure ($lbs_f/in^2$) | Flow (L/min) | Example 7 Pressure ($lbs_f/in^2$) | Flow (L/min) | Comment |
|---|---|---|---|---|---|
| 0 | 2.8 | 2.0 | 3.1 | 2.0 | |
| 0.75 | 2.8 | 2.0 | 3.1 | 2.0 | |
| 2.75 | 2.8 | 2.0 | 3.2 | 2.0 | |
| 17.25 | 2.8 | 2.0 | 3.2 | 1.76 | |
| 17.42 | 2.8 | 2.0 | 3.8 | 2.0 | |
| 19.00 | 2.8 | 2.0 | 4.0 | 2.0 | |
| 22.42 | 2.8 | 2.0 | 4.1 | 2.0 | |
| 25.00 | 2.8 | 2.0 | 4.4 | 2.0 | |
| 41.25 | 2.8 | 2.0 | 4.5 | 1.69 | |
| 41.50 | 2.8 | 2.0 | 5.5 | 2.0 | |
| 42.92 | 2.8 | 2.0 | 5.5 | 2.0 | |
| 49.00 | 2.8 | 2.0 | 5.9 | 2.0 | |
| 50.75 | 2.8 | 2.0 | 6.2 | 2.0 | |
| 67.75 | 2.8 | 1.88 | 6.8 | 1.67 | |
| 69.75 | 2.9 | 2.0 | 8.5 | 2.0 | |
| 88.75 | 2.9 | 1.88 | 8.7 | 1.5 | |
| 89.08 | 3.0 | 2.0 | 8.5 | 2.0 | Purged through valves 56 and 62 |
| 115.25 | 2.9 | 1.88 | 9.0 | 1.88 | |
| 115.42 | 3.0 | 2.0 | 9.6 | 2.0 | |
| 117.25 | 8.0 | 2.0 | 8.0 | 2.0 | Purged through |

TABLE V-continued

| Elapsed Time (hours) | Comp. Ex. 5 Pressure (lbs$_f$/in$^2$) | Flow (L/min) | Example 7 Pressure (lbs$_f$/in$^2$) | Flow (L/min) | Comment |
|---|---|---|---|---|---|
| | | | | | valves 56 and 62 |
| 118.00 | 9.5 | 2.0 | 8.5 | 2.0 | |
| 121.00 | 11.0 | 0.0066 | 9.5 | 1.76 | |
| 121.42 | 10.0 | 0.0121 | 9.0 | 2.0 | Purged through valves 56 and 62 |
| 138.75 | 10.8 | 0.0078 | 9.5 | 1.26 | |
| 139.25 | 10.8 | 0.0150 | 9.5 | 1.67 | Purged through valves 56 and 62 |
| 142.25 | 11.0 | 0.0029 | 9.5 | 1.30 | |
| 165.25 | 11.0 | 0.0014 | 9.8 | 1.10 | |
| 165.75 | 11.0 | 0.0009 | 9.8 | 1.56 | Purged through valves 56 and 62 |
| 168.25 | 11.0 | 0 | 9.8 | 1.38 | |
| 168.75 | | | 8.0 | 1.06 | Purged through valve 56 |
| 188.50 | | | 8.0 | .96 | |
| 193.08 | | | 8.0 | 0.93 | |
| 212.00 | | | 8.0 | 0.78 | |
| 212.31 | | | 8.0 | 0.91 | |
| 213.75 | | | 8.0 | 0.86 | |

The above data reveal that the differential pressure across the flat sheet membrane remained steady for about 90 hours then rose rapidly. At 121 hours, the flat sheet membrane was substantially completely clogged. Flow through the flat sheet membrane began to show signs of slowing down at about 68 hours. It dropped off to nearly zero at 121 hours. The pressure differential across the coated, hollow fiber module gradually increased, starting very soon after the start of the test. Initially, the hollow fiber module pressure differential was larger than that of the flat sheet as might be expected from a continuous, non-porous barrier to gas flow in comparison to a porous membrane structure.

Starting at about 89 hours, air was blown out through the excess oily air valves 56 and 62 for five minutes. This was done to attempt to clean out any oil that might have accumulated in the gas filters. During these "blow outs" no liquid oil was observed to discharge from the flat sheet membrane holder while liquid oil flowed from the fiber module. These phenomena suggested that oil penetrated the flat sheet but was prevented from passing through the hollow fibers. The module had a transparent case. Visual inspection during the trial showed that no liquid oil penetrated the fibers and settled in the shell side cavity. However, when the flat sheet holder was opened at the end of the test, liquid oil was found in the membrane and on the top surface of the membrane. These observations confirmed the suggestion with regard to penetration of oil through the membrane structures.

As a result of blowing air out of the excess oily air lines, the flows of both gas filters directly returned to the goal amounts of 2.0 L/min. This purging procedure was repeated five additional times. In four of the five instances, flow through the hollow fiber module increased significantly. The flat sheet membrane structure did not respond to any of the subsequent purges. The permeate air flow through the hollow fiber module remained above 50% of starting goal for over 168 hours. After 213 hours at conclusion of the test, the hollow fiber module delivered 46% of goal flow. The pressure drop across the hollow fiber module was lower than the peak pressure differential across the flat sheet membrane. These data demonstrate that the novel membrane structure with a continuous non-porous barrier of gas permeable membrane will resist clogging by oil significantly longer than will a porous membrane structure. Furthermore, the non-porous membrane structure can be cleaned repeatedly to boost gas flow.

Example 8 and Comparative Example 6

A 47 diameter sample of fresh porous membrane from Comp. Ex. 3 was installed in a flat sheet membrane holder (Comparative Example 6). Ports 68 and 69 (FIG. 6) were closed and oil O-2 was poured into port 70 to fill the interior of the holder. Similarly, valve 56 (FIG. 5) of the hollow fiber module of Ex. 6 was closed and the tube side cavity of the module was filled with oil O-2. The gas filters were held liquid-full for one hour. The oil was drained from the gas filters which were installed in the testing apparatus of FIG. 5. Excess air valves 62 and 56 were opened and pump 80 was started. Air was swept through the gas filters for 10 minutes to remove residual oil. Valves 62 and 56 were closed and valves 51, 52 and 53 were adjusted to control pressure on gauges 58 and 59 to 5 lbs$_f$/in$^2$. Data from this experiment is shown in Table VI.

TABLE IV

| Elapsed Time (hours) | Comp. Ex. 6 Pressure (lbs$_f$/in$^2$) | Flow (L/min) | Example 8 Pressure (lbs$_f$/in$^2$) | Flow (L/min) | Comment |
|---|---|---|---|---|---|
| 0.17 | 5.0 | 0.39 | 5.0 | 1.20 | |
| 0.67 | 5.0 | 0.22 | 5.0 | 1.34 | |
| 1.67 | 5.0 | 0.104 | 5.0 | 1.46 | |
| 2.42 | 5.0 | 0.04 | 5.0 | 1.46 | |
| 24.67 | 5.0 | 0.00 | 5.0 | 1.17 | |
| 24.92 | 5.0 | 0.00 | 5.0 | 1.30 | Purged through valves 56 and 62 |

This experiment demonstrates that the novel membrane structure with a continuous, non-porous layer of oleophobic, gas permeable polymer provided superior oil wetting resistance compared to a microporous structure coated with the same polymer. The gas flow through the novel hollow fiber module was high and stable for more than 24 hours. The conventional membrane structure clogged after less than three hours.

Example 9

A 0.1 wt % stock solution was prepared by adding 1.164 g of Polymer B to 900 ml (1620 g) of FC-75 in a glass bottle and shaking manually for about 10 minutes. The solution was agitated by rolling the bottle on a roll mill under a heat lamp overnight. A 0.005 wt % coating solution was prepared by diluting 50 ml of the stock solution with 950 ml of FC-75 in a clean bottle and shaking for about 5 minutes. The dilution was repeated to produce 4L of coating solution.

Figure 4:
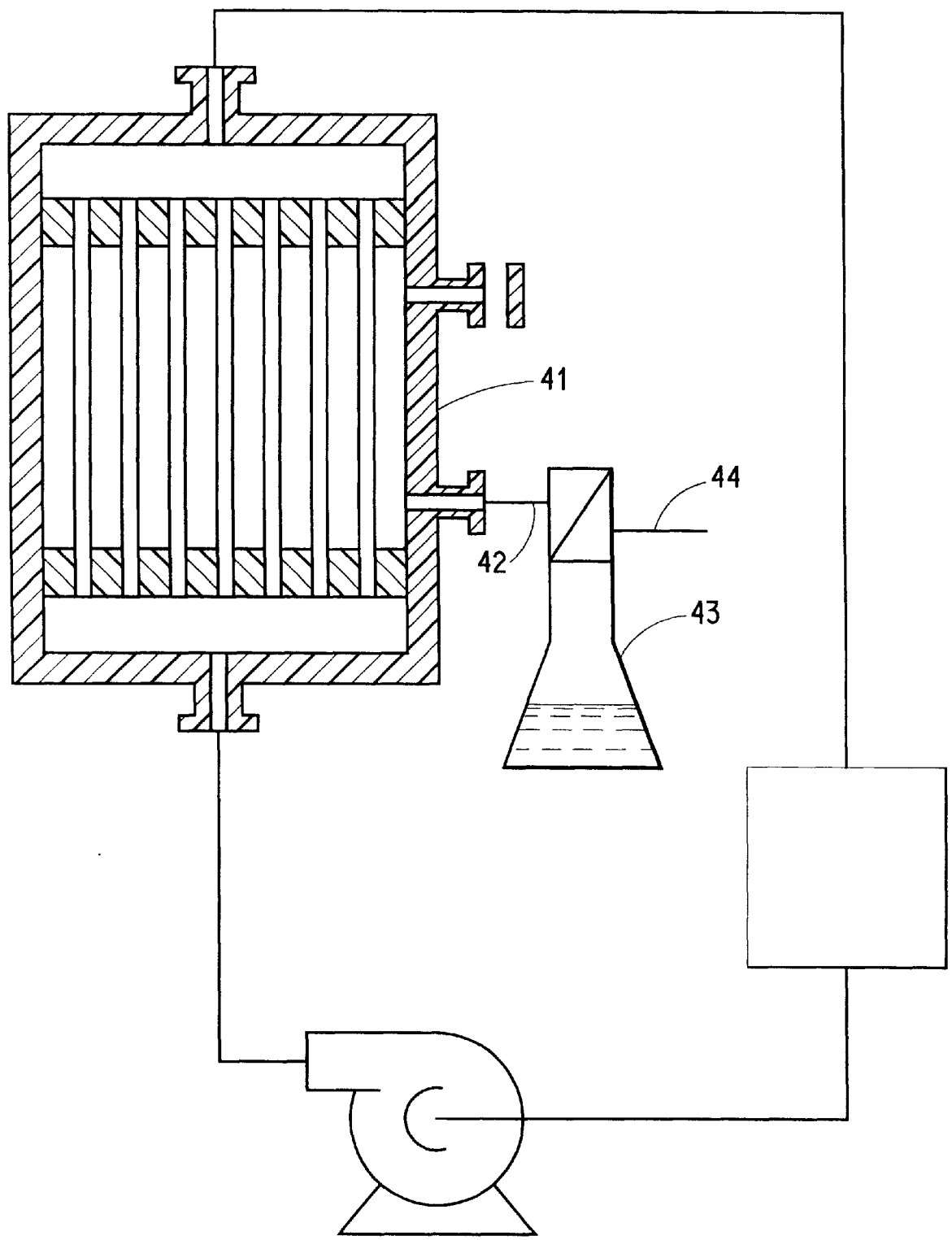
FIG. 4 is a schematic diagram of another apparatus useful for coating a thin layer of gas permeable polymer onto hollow fibers of a gas filter module according to the process of the present invention.

A "MiniKros" hollow fiber module (Spectrum, Inc. part No. S555 001 HF-2) with a polysulfone casing of 3.2 cm inner diameter containing about 1,153 microporous polysulfone fibers of 460 μm inner diameter and 640 μm outer diameter was mounted in a coating apparatus as shown in FIG. 4, but horizontally. The porosity of the polysulfone fibers was rated at 50,000 MWCO. The effective length of the polysulfone fibers was 20 cm which provided a total filter surface area of 3895 cm$^2$.

The same pump and feed tank as in Example 2 were used. The two shell side ports were manifolded using silicone rubber tubing connected in a "Y" configuration. The common tube was connected to a 1000 ml capacity KIMAX filter flask. The vapor space of the filter flask was vented through exhaust tube 44 to a vacuum source (not shown) consisting of a 36.8 cm long by 3.8 cm inner diameter two-piece vacuum trap submerged in ice and a Welch Duo-seal laboratory vacuum pump. Air was bled into the trap with an adjustable valve (not shown) to control the filter flask at a selected pressure.

Initially 1800 ml of the coating solution was charged to the feed tank. Pressure of the filter flask was set to a vacuum of 30 cm Hg absolute. The solution circulation pump was started which caused flow of coating solution into the module. Permeate began to collect in the filter flask. An additional 1700 ml of coating solution was charged to the feed tank after the coating solution inventory level dropped sufficiently to make room.

Three minutes after starting solution recirculation the filter flask was filled. A valve in the vacuum line (44, FIG. 4) was shut temporarily while an empty flask was installed. Then the valve was opened and filtration was resumed. The filter flask change operation was repeated at 7 minutes and again at 11 minutes from start-up. The feed tank was empty after 14 minutes of operation and the solution circulation pump was stopped. The module was disconnected from the solution apparatus and drained of liquid. The fibers were dried with 30 L/min. nitrogen purged through the tube side for 5.5 hours as in Example 2.

Viscosity of the permeate was checked subsequently as in Example 2 and found to be the same as the viscosity of FC-75, i.e., 225 seconds drop time through No. 191 viscometer. By the measurement methods described in Example 2, the average thickness and the $O_2/N_2$ selectivity of the Polymer B layer on the hollow fibers were found to be 0.45 μm and 2.59, respectively.

Example 10

A hollow fiber module was coated as in Example 9, except for the following changes. A 0.5 wt % coating solution of Polymer A was used. The coating solution was prepared by adding 500 ml of FC-75 to 500 ml of stock solution prepared in Example 2 and shaking by hand for about 5 minutes. The hollow fiber module used was a "MiniKros Sampler" (Spectrum, Inc. Special Lot No. 032596-1) which had a 1.6 cm inner diameter polysulfone casing and 1000 microporous polypropylene fibers of 200 μm inner diameter and 250 μm outer diameter. The pore size of the polypropylene fibers was nominally 0.05 μm. The feed tank was filled with 500 ml of coating solution and pressure of the filter flask was set to a vacuum of 5 cm Hg absolute. Then the module was mounted vertically in the recirculation apparatus. The solution circulation pump was started which caused flow of coating solution into the bottom of the module at a rate that filled the tubes in 4 seconds. After recirculating coating solution for 9 minutes and 15 seconds, the pump was stopped. The module was disconnected from the recirculation apparatus and drained of liquid. The fibers were dried with 1 L/min of nitrogen for 5.5 hours purging through the tube side. $O_2/N_2$ selectivity of the coated module was measured to be 1.81 and the thickness of the non-porous polymer layer on the interior of the fibers was determined to be 0.9 μm.

Example 11

A hollow fiber module was coated on the outside of the fibers, i.e. the fiber shell side. The procedure was similar to that of Example 10 in that the coating solution was drawn through the hollow fibers under vacuum. A total of about 200 ml of 0.1 wt % Polymer B stock solution of made as in Example 9 was used for the coating solution. A "MiniKros Sampler" (Spectrum, Inc. Specal Lot No. 081696-2) which had 1190 microporous polypropylene fibers of 0.05 μm pore size and effective length of 21.3 cm was mounted horizontally in the recirculation apparatus. The coating solution was introduced into one of the shell side ports and returned to the feed tank via the other shell side port. The two tube side ports were manifolded with a "Y" connector and the common tubing was connected to the permeate collection flask of the vacuum system. Thus the FC-75 was drawn from solution on the shell side and through the microporous fibers into the bore of the fibers. The vacuum on the tube side was maintained at 500 mm Hg absolute pressure.

Circulation was stopped when the feed tank had emptied. The module was disconnected from the circulation apparatus and liquid was drained. Nitrogen was purged through the shell side for 20 minutes at 8 L/min. An additional 0.5 L/min. nitrogen drying gas sweep was blown through the shell side for 8 hours to continue drying. After coating, the $O_2/N_2$ selectivity of the module was determined to be 1.72 and the coating thickness was 0.3 μm.

Example 12

A module containing about 99 microporous polyvinylidene fluoride ("PVDF") hollow fibers was coated with Polymer A substantially as in Example 2 and with the following changes. The module was a Spectrum, Inc. S555001HF-12 "Krosflow" model with a 1.6 cm inner diameter. The fibers were 1 mm inner diameter and 1.2 mm outer diameter and the pore size rating of the fibers was 500,000 MWCO. Overall length of the fibers was 13.6 cm and the effective length was 12.5 cm.

The module was mounted horizontally in the circulation apparatus with silicone rubber tubing from each of the shell side ports manifolded with a "Y" connector. Instead of returning permeate to the feed tank, the common discharge line from the Y connector was lead to a collection bottle. Two hundred ml of coating solution was charged to the feed tank which had a 1L capacity. The pump was operated at about 5 ml/sec flow rate. The return line from the tube side exit to the tank was restricted with a hose clamp to adjust return flow to about 3.5 ml/sec. Thus about 1.5 ml/sec permeate was collected. When the feed tank had emptied, the pump was stopped. Liquid was emptied from the module and low pressure nitrogen gas was purged through the tube side at a rate of 2 L/min for 4 hours.

After coating, the $O_2/N_2$ selectivity of the module was determined to be 1.87 and the coating thickness was 2.70 μm.

Although specific forms of the invention have been selected for illustration in the drawings and examples, and the preceding description is drawn in specific terms for the purpose of describing these forms of the invention, this description is not intended to limit the scope of the invention which is defined in the claims.

Comparative Example 6

An 11.5 cm² filter surface area, 12 hollow fiber module was coated on the inside of the fibers with a layer of "Matrimid 5218" polyimide polymer from Ciba Geigy using the procedure described in Example 9. The hollow fibers were microporous polypropylene of porosity of about 0.05 μm which corresponds to a MWCO of about 100,000. The polyimide had a molecular weight of 30,000 and inherent viscosity of 0.6 in n-methyl pyrrolidone. The polymer was dissolved at 1.5 wt % in clear dimethyl formamide to make 100 ml of orange colored, coating solution. The coating solution was drawn through the fibers under vacuum of about 380 mm Hg absolute pressure. It was observed that the permeate liquid was orange colored which indicated that polymer was not effectively filtered by the microporous hollow fibers.

Each of nitrogen and oxygen had a flux through the uncoated module of about 65,000 GPU. After coating, both nitrogen and oxygen fluxes were reduced to 14,700. The $O_2/N_2$ selectivity remained approximately equal to unity which indicated that a continuous non-porous layer of gas permeable polymer had not been formed on the polypropylene substrate. Non-porous polyimide has an $O_2/N_2$ selectivity of greater than 5.0. This example demonstrates the importance of establishing a relationship between the molecular weight of the dissolved polymer and the pore size of the substrate such that the substrate effectively filters the polymer to create a continuous non-porous layer on the substrate according to the present invention.

Examples 13–14 and Comparative Examples 7–8

Four modules of same construction as those of Examples 4–6 were coated on the inside of the polysulfone hollow fibers with ultra-thin layers of Polymer A according to the method of this invention. Pertinent data are presented in table VII. The primary difference among these examples is that the solvent was evaporated from the comparative examples by drying in a vacuum oven overnight at 100° C. while the operative examples were swept with nitrogen gas at the stated flow rates overnight.

The average coating thickness was calculated from measured flow through the fibers and known permeability of the coating composition. The average inside diameter of the fibers was measured through hydraulic calculations based upon measured flow at measured pressure drop across the bank of tubes. The uncoated fibers had average inside diameter of 420 μm. The data show that despite very thin coating of much less than 1 μm in all cases, the average inside diameter of the comparative example module fibers was significantly less than the expected dimension of about 418 μm. The difference is believed attributed to non-uniform thickness of the coating on the inside of the fibers. When the solvent was removed by gas sweeping at high rate, as in Examples 13 and 14, the observed average fiber diameter was much closer to the expected dimension. These examples thus demonstrate that a high flow of sweep gas is important to achieving the desired coating geometry according to the present invention.

TABLE VII

| Example | Method | Coating Solution Conc'n. (wt %) | O2/N2 Select-ivity | Non-porous Layer Thickness (μm) | Coated Fiber Inner Diameter (μm) |
|---|---|---|---|---|---|
| Comp. Ex 7 | Vacuum Oven | 0.20 | 1.8 | 0.16 | 372 |
| Comp. Ex. 8 | Vacuum Oven | 0.30 | 1.27 | 0.05 | 363 |
| Ex. 13 | 4 L/min. Nitrogen Sweep | 0.15 | 1.57 | 0.12 | 410 |

TABLE VII-continued

| Example | Method | Coating Solution Conc'n. (wt %) | O2/N2 Select-ivity | Non-porous Layer Thickness (μm) | Coated Fiber Inner Diameter (μm) |
|---|---|---|---|---|---|
| Ex. 14 | 2 L/min. Nitrogen Sweep | 0.20 | 1.89 | 0.5 | 413 |

What is claimed is:

1. A process for making a membrane structure comprising the steps of:

(a) dissolving a gas permeable polymer in a solvent to obtain a coating solution;

(b) selecting a microporous substrate of a pore size effective for filtering dissolved polymer from the coating solution, the substrate having a first side, and a second side;

(c) contacting the first side of the microporous substrate with the coating solution;

(d) making the solvent flow through the microporous substrate to the second side;

(e) removing coating solution and solvent from the membrane structure; and (f) evaporating solvent from the membrane structure, thereby forming a continuous, non-porous layer of the gas permeable polymer on the first side wherein the gas permeable polymer is an amorphous copolymer of perfluoro-2,2-dimethyl-1,3-dioxole having a permeability to oxygen of at least 100 barrers at a temperature below the glass transition temperature of the amorphous copolymer.

2. The invention of claim 1 wherein steps (c)–(f) are repeated until the non-porous layer of the gas permeable polymer on the microporous substrate is a preselected thickness.

3. The invention of claim 1 wherein the non-porous layer is about 0.01 to about 25 μm thick.

4. The process of claim 1 in which the membrane structure is other than a hollow fiber.

5. The invention of claim 1 wherein the amorphous copolymer is a copolymer of perfluoro-2,2-dimethyl-1,3-dioxole and a complementary amount of at least one monomer selected from the group consisting of tetrafluoroethylene, perfluoromethyl vinyl ether, vinylidene fluoride, hexafluoropropylene and chlorotrifluoroethylene.

6. The invention of claim 5 wherein the amorphous copolymer is a dipolymer of perfluoro-2,2-dimethyl-1,3-dioxole and tetrafluoroethylene.

7. The invention of claim 6 wherein the dipolymer comprises 50–95 mole % polymerized perfluoro-2,2-dimethyl-1,3-dioxole.

8. The invention of claim 7 wherein the membrane structure has an oxygen/nitrogen selectivity of at least about 1.5:1.

9. The invention of claim 1 wherein the microporous substrate is of a polymer selected from the group consisting of polyolefin; fluorinated polyolefin; polysulfone; cellulose ester polymer; a copolymer of olefin, a copolymer of fluorinated olefin; a polysulfone copolymer; a cellulose ester copolymer and a mixture of them.

10. The invention of claim 9 wherein the microporous substrate is polypropylene.

11. The invention of claim 9 wherein the microporous substrate is polyvinylidene fluoride.

12. The invention of claim 9 wherein the substrate has a molecular weight cut off less than the weight average molecular weight of the gas permeable polymer.

13. The invention of claim 12 wherein the molecular weight cut off is at most 50,000.

14. The invention of claim 12 wherein the pore size of the substrate is effective to pass oxygen gas through uncoated substrate at a rate of at least five times the flux of oxygen gas through the non-porous layer.

15. The invention of claim 14 wherein the pore size of the substrate is effective to transfer at least 10,000 gas permeation units of oxygen gas.

16. The invention of claim 1 wherein the microporous substrate is a hollow fiber.

17. The invention of claim 1 wherein at most about 1 wt % gas permeable polymer is dissolved in the coating solution.

18. The invention of claim 1 wherein the evaporating step includes blowing a gas in contact with the non-porous layer at a rate effective to dry the non-porous layer to a uniform thickness on the membrane structure.

19. A process for making a gas filter comprising the steps of:
(a) dissolving a gas permeable polymer in a solvent to obtain a coating solution;
(b) providing a filter module including
(1) an elongated casing having two ends, the casing defining a shell side cavity;
(2) a first tube sheet at one end of the casing having a first tube sheet outboard face;
(3) a second tube sheet at the other end of the casing having a second tube sheet outboard face;
(4) a plurality of open ended, microporous hollow fibers extending in substantially parallel alignment within the casing from the first tube sheet outboard face to the second tube sheet outboard face, the hollow fibers collectively defining a tube side cavity; wherein the pore size of the hollow fibers is effective to filter dissolved polymer from the coating solution; and
(5) at least one shell side port through the casing;
(c) causing the coating solution to flow through one of the shell side cavity and the tube side cavity;
(d) making the solvent flow from the coating solution through the microporous hollow fibers to the other of the shell side cavity and the tube side cavity;
(e) draining coating solution and solvent from the module; and
(f) evaporating solvent from the hollow fibers thereby forming a continuous, non-porous layer of the gas permeable polymer on one side of the hollow fibers.

20. The invention of claim 19 further comprising the step of positioning the filter module to orient the microporous hollow fibers vertically before the step of causing the coating solution to flow and wherein the coating solution is caused to flow upwards through the tube side cavity.

21. The invention of claim 20 wherein the evaporating solvent step includes blowing an inert gas through the tube side cavity at a flow rate effective to evaporate the solvent without occluding a major fraction of the hollow fibers with the polymer.

22. The invention of claim 19 wherein steps (c)–(f) are repeated until the non-porous layer of the gas permeable polymer on the hollow fibers is a preselected thickness.

23. The invention of claim 19 wherein the gas permeable polymer is an amorphous copolymer of perfluoro-2,2-dimethyl-1,3-dioxole having a permeability to oxygen of at least 100 barrers at a temperature below the glass transition temperature of the amorphous copolymer.

24. The invention of claim 23 wherein the amorphous copolymer is a copolymer of perfluoro-2,2-dimethyl-1,3-dioxole and a complementary amount of at least one monomer selected from the group consisting of tetrafluoroethylene, perfluoromethyl vinyl ether, vinylidene fluoride, hexafluoropropylene and chlorotrifluoroethylene.

25. The invention of claim 24 wherein the amorphous copolymer is a dipolymer of perfluoro-2,2-dimethyl-1,3-dioxole and tetrafluoroethylene.

26. The invention of claim 25 wherein the dipolymer comprises 50–95 mole % polymerized perfluoro-2,2-dimethyl-1,3-dioxole.

27. The invention of claim 19 wherein the gas filter has an oxygen/nitrogen selectivity of at least about 1.5:1.

28. The invention of claim 19 wherein the hollow fibers are of a polymer selected from the group consisting of polyolefin; fluorinated polyolefin; polysulfone; cellulose ester polymer; a copolymer of olefin, a copolymer of fluorinated olefin; a polysulfone copolymer; a cellulose ester copolymer and a mixture of them.

29. The invention of claim 28 wherein the hollow fibers are polypropylene.

30. The invention of claim 28 wherein the hollow fibers are polyvinylidene fluoride.

31. The invention of claim 28 wherein the hollow fibers have a molecular weight cut off less than the weight average molecular weight of the gas permeable polymer.

32. The invention of claim 31 wherein the molecular weight cut off is at most 50,000.

33. The invention of claim 31 wherein the pore size of the hollow fibers is effective to transfer oxygen gas at least five times the flux of oxygen gas through the non-porous layer.

34. The invention of claim 33 wherein the pore size of the hollow fibers is effective to transfer at least 10,000 gas permeation units of oxygen gas.

35. The invention of claim 19 wherein the pore size of the hollow fibers is about 0.005 –0.1 $\mu$m.

36. The invention of claim 19 wherein the non-porous layer is about 0.01 to about 25 $\mu$m thick.

37. The process of claim 4 in which the membrane structure is in the form of a flat sheet.

38. A process for making a membrane structure comprising the steps of:
(a) dissolving a gas permeable polymer in a solvent to obtain a coating solution;
(b) selecting a microporous substrate of a pore size effective for filtering dissolved polymer from the coating solution, the substrate having a first side, and a second side;
(c) contacting the first side of the microporous substrate with the coating solution;
(d) making the solvent flow through the microporous substrate to the second side;
(e) removing coating solution and solvent from the membrane structure; and
(f) evaporating solvent from the membrane structure, thereby forming a continuous, non-porous layer of the gas permeable polymer on the first side,
in which the microporous structure comprises a hollow fiber defining an interior surface and an exterior surface, the first side is the interior surface and the second side is the exterior surface.

39. The invention of claim 38 wherein steps (c)–(f) are repeated until the non-porous layer of the gas permeable polymer on the microporous substrate is a preselected thickness.

40. The invention of claim 38 wherein the non-porous layer is about 0.01 to about 25 μm thick.

41. The invention of claim 38 wherein the microporous substrate is of a polymer selected from the group consisting of polyolefin; fluorinated polyolefin; polysulfone; cellulose ester polymer; a copolymer of olefin, a copolymer of fluorinated olefin; a polysulfone copolymer; a cellulose ester copolymer and a mixture of them.

42. The invention of claim 41 wherein the microporous substrate is polypropylene.

43. The invention of claim 41 wherein the microporous substrate is polyvinylidene fluoride.

44. The invention of claim 41 wherein the substrate has a molecular weight cut off less than the weight average molecular weight of the gas permeable polymer.

45. The invention of claim 44 wherein the molecular weight cut off is at most 50,000.

46. The invention of claimed 44 wherein the pore size of the substrate is effective to pass oxygen gas through uncoated substrate at a rate of at least five times the flux of oxygen gas through the non-porous layer.

47. The invention of claim 46 wherein the pore size of the substrate is effective to transfer at least 10,000 gas permeation units of oxygen gas.

48. The invention of claim 38 wherein at most about 1 wt % gas permeable polymer is dissolved in the coating solution.

49. The invention of claim 38 wherein the evaporating step includes blowing a gas in contact with the non-porous layer at a rate effective to dry the non-porous layer to a uniform thickness on the membrane structure.

* * * * *

UNITED STATES PATENT AND TRADEMARK OFFICE
CERTIFICATE OF CORRECTION

PATENT NO. : 5,914,154
DATED : June 22, 1999
INVENTOR(S) : Stuart Nemser

It is certified that error appears in the above-identified patent and that said Letters Patent is hereby corrected as shown below:

Column 1,
Before "FIELD OF THE INVENTION" insert the following paragraph:

-- This invention was made with Government support under contract number 9560667 awarded by the National Science Foundation. The Government has certain rights in the invention. --

Signed and Sealed this

Twenty-fifth Day of December, 2001

*Attest:*

JAMES E. ROGAN
*Attesting Officer*        *Director of the United States Patent and Trademark Office*